United States Patent
Lee et al.

(10) Patent No.: US 10,538,635 B2
(45) Date of Patent: Jan. 21, 2020

(54) SOLID STATE ELECTRODES AND SENSORS

(71) Applicant: Parker-Hannifin Corporation, Cleveland, OH (US)

(72) Inventors: Eric K. Lee, Acton, MA (US); Boaz Vilozny, Santa Cruz, CA (US); James Andrew, Los Altos, CA (US)

(*) Notice: Subject to any disclaimer, the term of this patent is extended or adjusted under 35 U.S.C. 154(b) by 343 days.

(21) Appl. No.: 15/318,269

(22) PCT Filed: Jun. 11, 2015

(86) PCT No.: PCT/US2015/035428
§ 371 (c)(1),
(2) Date: Dec. 12, 2016

(87) PCT Pub. No.: WO2015/191924
PCT Pub. Date: Dec. 17, 2015

(65) Prior Publication Data
US 2017/0101513 A1    Apr. 13, 2017

Related U.S. Application Data

(60) Provisional application No. 62/010,987, filed on Jun. 11, 2014.

(51) Int. Cl.
*C08J 3/075* (2006.01)
*G01N 27/30* (2006.01)
*G01N 27/416* (2006.01)

(52) U.S. Cl.
CPC ............ *C08J 3/075* (2013.01); *G01N 27/302* (2013.01); *C08J 2329/04* (2013.01); *G01N 27/4167* (2013.01)

(58) Field of Classification Search
CPC ............................ C08J 3/075; C08J 2329/04
See application file for complete search history.

(56) References Cited

U.S. PATENT DOCUMENTS

| 2004/0044094 A1* | 3/2004 | Garnett ........... C08F 2/46 522/1 |
| 2006/0025550 A1 | 2/2006 | Zuifang |
| 2012/0132544 A1 | 5/2012 | Lawrence et al. |

FOREIGN PATENT DOCUMENTS

| WO | WO2005066618 | 7/2005 |
| WO | WO2007034131 | 3/2007 |
| WO | WO2010104962 | 9/2010 |
| WO | WO2012018632 | 2/2012 |
| WO | WO-2015032314 A1 * | 3/2015 ............ C08J 3/075 |

OTHER PUBLICATIONS

Robinson, Kay L., et al., "A Vinylanthracene and Vinylferrocene-Containing Copylmer," VHC Publishers, Inc., vol. 18, No. 7, Apr. 1, 2006.

* cited by examiner

*Primary Examiner* — Susan D Leong
(74) *Attorney, Agent, or Firm* — David R. Conklin; Kirton McConkie

(57) ABSTRACT

Analyte-insensitive materials comprising polymerizable monomers suitable for use in forming a hydrophilic, cross-linked gel comprising on the surface of a substrate for an electrode.

6 Claims, 10 Drawing Sheets

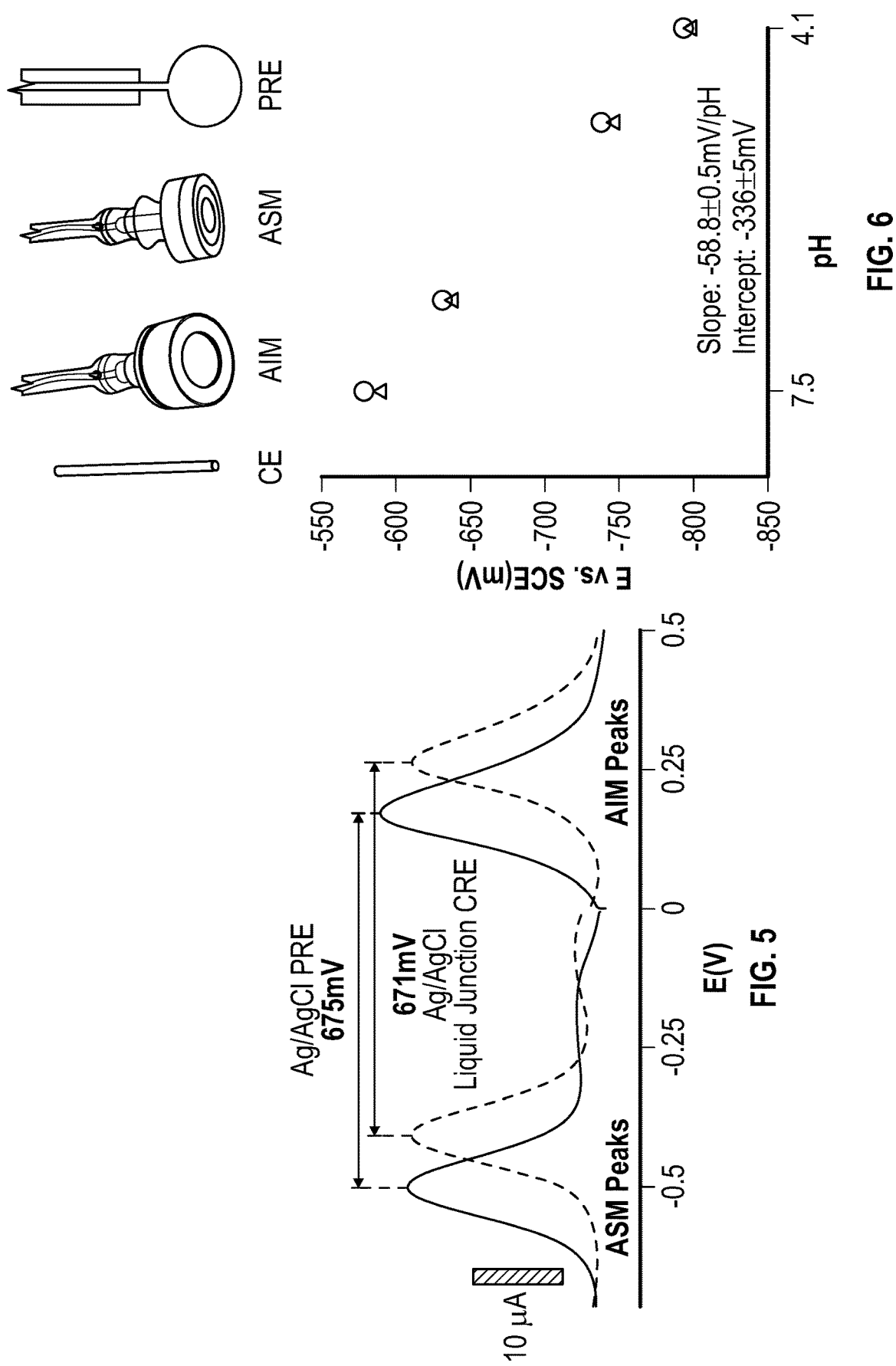

Electrodes

SOLID STATE ELECTRODES AND SENSORS

This application is a National Stage of International Application No. PCT/US2015/035428, filed Jun. 11, 2015, and entitled SOLID STATE ELECTRODES AND SENSORS, which claims the benefit of U.S. Provisional Application No. 62/010,987, filed Jun. 11, 2014. This application claims priority to and incorporates herein by reference the above-referenced applications in their entirety.

BACKGROUND OF THE INVENTION

Field of the Invention

The present invention provides solid-state electrodes, including "indicator electrodes" ("IEs") that utilize a redox-active analyte-insensitive material ("AIM"), and working electrodes ("WEs") that utilize a redox-active analyte-sensitive material ("ASM"), for use in electrochemical analysis, including pH measurement, as well as methods for making and using the materials of the invention, and the electrodes, sensors, and devices comprising them. In one embodiment, an AIM is incorporated into an IE used in conjunction with a pseudo reference electrode ("PRE") and an ASM that serves as a WE. The IE corrects drifts in the pH reading (or other analyte measurement) caused by changes in PRE potential, thereby improving the accuracy of the measurement and eliminating the need for calibration processes required for other types of analyte sensors. Accordingly, the invention relates to the fields of chemistry and electrochemistry in particular and to the field of analyte measurement, particularly pH measurement, and all the various fields where such measurements are made.

Description of Related Disclosures

Electrodes and analyte-sensing devices based on AIM and/or ASM electrochemistry have previously been described. See U.S. Pat. Nos. 4,857,167; 5,223,117; 7,901,555; 8,177,958; 8,197,650; 8,506,779; 8,562,797; 8,877,037; 8,956,519; 8,961,754, incorporated herein by reference. See also PCT Pub. Nos. 2010/026842, 2010/028726, 2011/045385, 2013/112767, and 2013/134582, and 2014/106066, each of which is incorporated herein by reference. Electrodes utilizing the AIM ferrocene are described in Lafitte et al. (2008), *Electrochemistry Communications*, 10(12), 1831-1834; Hickman et al. (1991), *Science*, 252 (5006), 688-691; Robinson and Lawrence (2006), *Electroanalysis*, 18 (2006) 677-683, and Robinson and Lawrence (2008), *Analytical Sciences* 24. 339-343. While ferrocene hydrogels have been previously described in the art, these teachings and materials are limited to use as redox mediators for the purpose of transducing signals from a separate sensing element. Further, these references fail to teach or contemplate the physical properties of the ferrocene hydrogels discussed herein. Further, the present invention provides ferrocene hydrogel pH sensing elements that detect and report a reference redox signal.

Electrochemical sensors utilizing ASM/AIM and square wave voltammetry (SWV), sometimes called "voltammetric sensors," have been hailed as providing an opportunity for "calibration-free" sensing (meaning that the sensor does not have to calibrated by the end user), especially for pH measurement. In these sensors, a pH-sensitive signal, generated by the WE, and a pH-insensitive signal, generated by the IE, are generated contemporaneously by a given analyte using SWV methods. If the analyte is hydronium ion (for pH measurement), the ASM WE changes potential in response to changes in hydronium ion concentration, whereas an ideal AIM for an IE in a pH meter generates a potential that is constant regardless of changes in the pH. Both of these potentials are measured relative to a reference electrode (RE) potential, as shown in FIG. 1. In this way, the difference between the ASM and AIM signals can be correlated to pH, or other analyte, and this difference ideally is independent of the absolute potential of the RE, which may be either a conventional reference electrode ("CRE") or a PRE. Thus, for voltammetric sensors, changes in the RE have much less influence on the result than in conventional potentiometric pH sensors, which rely entirely on the stability and accuracy of the RE. Indeed, for voltammetric sensors, the simpler PRE (for example, a solid Ag/AgCl composition) may be used in place of a CRE (such as a Ag/AgCl or calomel CRE that is encased in a reference solution).

The need for calibration-free sensor technology remains, however, as none of the sensors referred to as "calibration-free" have proven to be so in practice and/or exhibit deficiencies in accuracy, signal strength, and/or durability. For example, previous self-calibrating sensors using ferrocene (Fc) as an internal reference electrode exhibited poor stability over time, and the Fc was sufficiently pH-insensitive only over a limited pH range. Any pH sensitivity decreases the precision of any required calibration and limits the reliability of the test result.

In terms of sensitivity, AIM electrodes (IEs) in the prior art based on Fc typically exhibit weaker, relatively noisy signals. In addition, the IEs and WEs of the prior art generate relatively weak and/or unstable signals, particularly under rigorous test conditions. Thus, a need remains for improved materials and methods for analyte sensing using an ASM-based WE and an AIM-based IE. The present invention meets this need.

SUMMARY OF THE INVENTION

It is a first object of the invention to provide new and useful components of pH meters, including WEs and IEs, as well as complete sensors that can be used to measure pH under a wide variety of conditions, heretofore not possible with the technology and devices of the prior art. In a preferred embodiment, the pH sensor of the invention is a small, compact, solid-state sensor that is wet-dry reversible and which comprises an AIM-based IE in which the ASM of the WE and the AIM of the IE is incorporated into a cross-linked, hydrogel matrix non-covalently attached to a conductive substrate, such as carbon, doped silicon, modified silicon, or a conductive silicon derivative, or a conductive polymeric material.

In a first aspect, the present invention provides a material suitable for use as an AIM. In one embodiment, the material is a preparation of polymerizable monomers suitable for use in forming a hydrophilic, cross-linked gel comprising an AIM. In another embodiment, the material is a hydrophilic, cross-linked gel that comprises an AIM. In another embodiment, the material is a preparation of polymerizable monomers forming a solid buffer that is coated onto an ASM that is acting as an AIM.

In a second aspect, the present invention provides an electrode comprising a porous, conductive substrate to which is non-covalently attached a hydrophilic, cross-linked hydrogel that comprises an AIM or ASM. In one embodiment, the electrode is an indicator electrode (IE). In another embodiment, the electrode is a WE. In another embodiment, the electrode is a solid state replacement for a traditional glass probe of a pH meter.

In a third aspect, the present invention provides an analyte-sensing device comprising an IE composed of a hydrophilic, cross-linked hydrogel that comprises an AIM, which gel is non-covalently attached to a porous, conductive substrate, a working electrode (WE) comprising an ASM, and a RE. In one embodiment, the RE is a solid state PRE, such as solid mixture of silver and silver chloride (Ag/AgCl) or a chloridized silver surface. In one embodiment of the device, the ASM of the WE is similarly covalently attached to or stably entrapped within a hydrogel that is, in turn, non-covalently attached to a conductive substrate to form the WE. The conductive substrate may be porous or otherwise shaped or treated to facilitate adherence of the hydrogel matrix.

In a fourth aspect, the present invention provides a method of measuring electrode potentials from an ASM-containing WE and an AIM-containing IE, relative to an RE, such as a solid state PRE, and establishing a correlation between analyte concentration or level and the difference between the WE and IE potentials. In one embodiment, the correlation is used to derive the pH of an analyte sample.

In one embodiment, the present invention relates to improvements in a process for measuring an analyte using an analyte sensor comprising a first WE, wherein the first WE comprises a first set of redox species (the ASM), and wherein the first set of redox species comprises one or more redox species that are sensitive to said analyte; an IE, wherein the IE comprises a second set of redox species (the AIM), and wherein the second set of redox species comprises one or more redox species that are insensitive to said analyte; a counter electrode ("CE"); an RE, which may be a CRE or PRE; means for applying a square wave potential sweep between a first and a second pair of electrodes, wherein the first pair of electrodes comprises the first WE and the RE and the second pair of electrodes comprises the IE and the RE; and means for detecting relative shifts between a first peak and a second peak in a square wave voltammogram, wherein the first peak is produced by one of oxidation and reduction of the first set of redox species and the second peak is produced by one of oxidation and reduction of the second set of redox species, said improvement comprising use of an IE in which the second set of redox active species is not covalently attached to the surface of the IE but is instead entrapped, whether covalently, non-covalently, or both, in a polymeric material adhered to the IE surface. In another embodiment, the improvement relates to the use of a WE in which the first set of redox active species is not covalently attached to the surface of the WE but is instead entrapped, whether covalently, non-covalently, or both, in a polymeric material adhered to the WE surface. In another embodiment, the present invention provides a device comprising both the improved IE and improved WE.

BRIEF DESCRIPTION OF THE FIGURES

FIG. 5 shows the effect of changes in RE on a WE-IE pair of the invention as described in Example 1. The results demonstrate the WE-IE relationship is independent of the CRE.

FIG. 6 shows the calibration of a WE-IE pair in an all-solid-state sensor system, as described in Example 2.

DETAILED DESCRIPTION OF THE INVENTION

Figure 1:
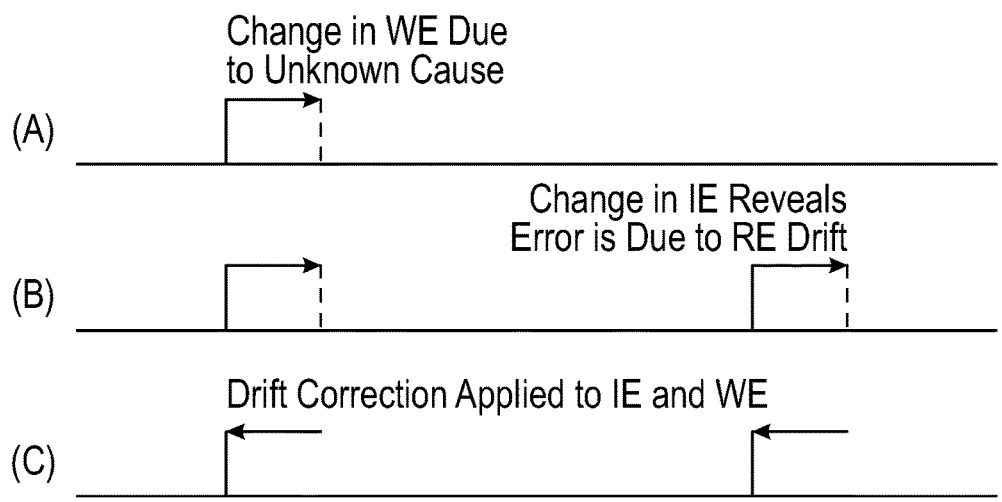
FIG. 1 shows schematically how, in an uncorrected voltammetric sensor, any drift in the RE potential results in a measurement error of an otherwise stable WE containing an analyte sensitive material (ASM) (illustrated in A of this Figure). This measurement error cannot be distinguished from a change in analyte concentration. If an analyte insensitive material (AIM) is used as an additional IE (illustrated in B of this Figure), any apparent drift must be attributed to the RE. Thus the drift in IE potential can be used to cancel the observed drift error in the working electrode (illustrated in C of this Figure). In this way, the difference in WE and IE potentials is effectively dissociated from changes in the properties or identity of the RE, and the sensor provides a more precise measure of the analyte.

AIM-based indicator electrodes and ASM-based working electrodes in the prior art generally exhibit limited precision, poor stability, and, for AIM IEs, narrow pH-insensitivity range, and, for ASM WEs, narrow pH sensitivity. AIM moieties (e.g. ferrocene) in these prior art electrodes are attached to the substrate surface directly, typically through covalent attachment. For electrodes in which the AIM or ASM is covalently attached to the substrate surface, the effective concentration of AIM or ASM achievable is limited by the two-dimensional surface area of the substrate accessible for reaction/binding. The functional group density attainable is, moreover, usually lower than the density of reactive sites, which results in low signal levels and consequent uncertainty in electrode potential measurements.

Moreover, prior attempts to provide wholly solid state, wet-dry reversible pH sensors resulted in no commercial products; prior to the present invention, there still is no commercially available solid state pH meter based on AIM/ASM solid state technology. Prior attempts may have failed due to inability to generate sufficient signal strength at the WE; too rapid signal degradation during use or storage; insufficient sensitivity over a sufficiently broad pH range; insufficient robustness for analyte samples or other conditions of use. The present invention provides a variety of materials, methods, electrodes, sensors, and devices that overcome these limitations, first by providing hydrogel materials in which an ASM or AIM is covalently attached to or stably entrapped within a cross-linked, hydrophilic, polymeric matrix, termed a "Hydrogel Polymer Matrix" or "Hydrogel".

Hydrogel Polymer Matrix

In the IEs and WEs of the present invention, the AIM, which can be or comprise a ferrocene derivative, and the ASM, which can be or comprise an anthraquinone derivative, is covalently linked to or physically entrapped within a highly swollen, cross-linked hydrophilic polymer matrix (a "hydrogel") that is not covalently linked to the conductive substrate but rather adheres to it by non-covalent bonding. The three-dimensional hydrogel structure accommodates a much higher concentration of the AIM (or ASM) relative to that achieved in the prior art. The high water permeability of the hydrogel ensures rapid interaction between the AIM (or ASM) and the sample being tested for analyte concentration, which promotes fast response to sample changes. The AIM hydrogels and ASM hydrogels of the invention also exhibit good wet-dry reversibility, retaining physical integrity upon drying and rapidly restoring redox activity upon rewetting. The range of pH insensitivity of the pH sensors of the invention typically encompasses at least pH 2 to pH 10.

Ferrocene (Fc) has been described as a suitable AIM for use in an IE, but immobilization of ferrocene at high concentrations often results in small but significant pH sensitivity outside a narrow pH range. Consequently, the analyte-independent property of the AIM is only partially realized. For example, physically immobilizing polyvinylferrocene (an AIM with an inherently high functional group density) onto a substrate produces a low-resolution signal.

Figure 2:
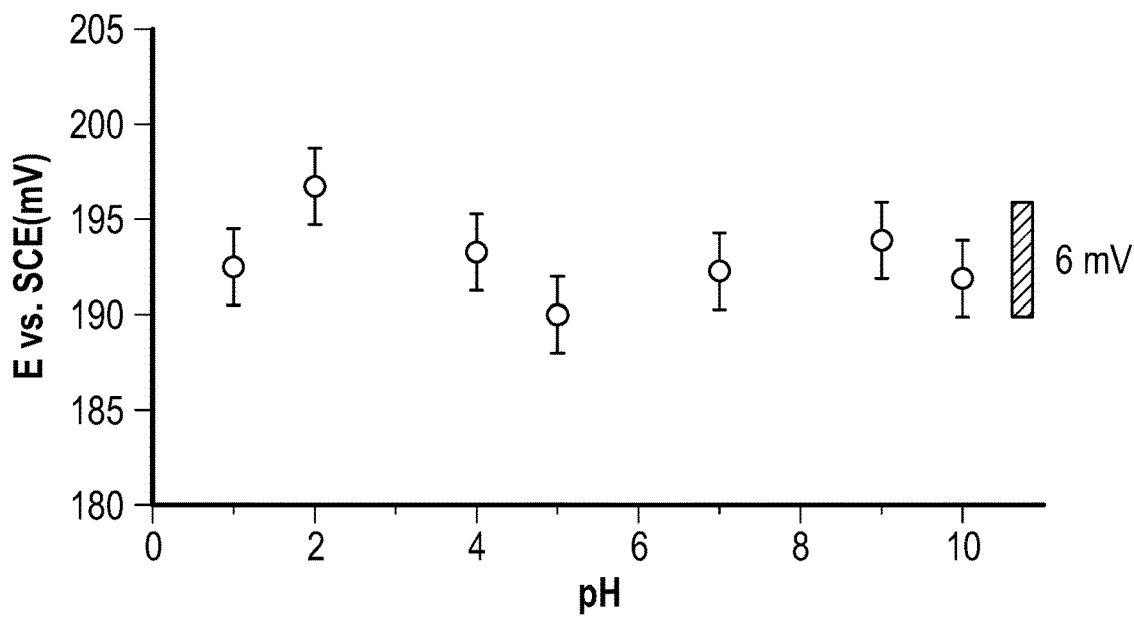
FIG. 2 shows data demonstrating that ferrocene methanol (Fc-MeOH) exhibits virtually the same square-wave peak potential in pH 1 to pH 10 buffer solutions. To generate this data, buffered solutions containing 1 mM Fc-MeOH and 100 mM sodium chloride were each scanned five times. Error bars reflect the standard deviation. It is an object of this invention to provide ferrocene hydrogels for use in IEs.

The present invention arose in part from the discovery that the pH-insensitivity range of certain ferrocene derivatives is substantially broader than in the solid state. For example, ferrocene methanol (Fc-MeOH, MW=216) exhibits virtually the same square-wave peak potential in pH 1 to 10 buffer solutions, as shown in FIG. 2. Thus, one object of the present invention is to preserve the native pH-insensitivity of the AIM and native pH-sensitivity of an ASM in embodiments of solid-state electrodes and sensors.

The materials provided by the present invention provide an AIM operating environment at the molecular level that mimics the environment of an AIM in free solution. A general approach of the invention is to incorporate an Fc derivative into a hydrated polymer matrix. The resulting polymer is in turn deposited on a conductive substrate to form an electrode. Preferably the Fc derivative is attached covalently to a hydrogel, defined as a cross-linked polymer matrix highly swollen by, but not soluble in, water. Typical hydrogels for use in accordance with the invention with Fc and Fc derivatives have equilibrium water contents much higher than the mass fraction of polymer. By comparison, polymers such as polyvinyl alcohol (suitable for use in forming WEs of the invention) rendered insoluble by thermal or chemical crosslinking have mass fractions of water comparable to or much less than the mass fraction of polymer. These are less suited as host polymers for the Fc unless a narrower pH-insensitivity range is acceptable.

For the present invention, suitable hydrogels are formulated as multi-component systems comprising one or more co-monomers that form three-dimensional networks of polymer chains capable of holding water in the space between chains. To form an AIM of the invention, in one embodiment at least one of the co-monomers is a reactive Fc derivative, such as vinylferrocene. Vinylferrocene (MW=212) is a reactive analog of Fc-MeOH, but is insoluble in water. However, it can be used in accordance with the invention in conjunction with other hydrophilic vinyl co-monomers and cross-linkers to form hydrogels based on polyacrylates, polyacrylamides, their polyether derivatives, and numerous others well known in the art. Formulating vinylferrocene as the minority component and other hydrophilic co-monomers as majority components serves the purpose of solvating the vinylferrocene and provides it with the hydration environment favorable to preserving its pH-insensitivity. In the preferred embodiment, AIM hydrogels are formulated such that 80% of the swollen gel mass is water. In some embodiments, AIM hydrogels are formulated such that 85 to 95% of the swollen gel mass is water.

The composition of the AIM-containing hydrogel can be described in terms of the polymer matrix, regardless of whether it is dry or hydrated. The present invention articulates two properties of the matrix which affect AIM performance: These are the mole percent (or mol %) AIM unit as a percentage of the total polymer units, and the mol % crosslinker as a percentage of the total polymer units. For the present invention, a monomer is considered a molecule with a pendant polymerizable group. A crosslinker is a molecule having two polymerizable groups. Both the mol % AIM and mol % crosslinker are determined by the stoichiometric amounts of monomers used, assuming the polymerization reaction goes to completion and all monomers are incorporated into the polymer chain.

In one embodiment of the invention, the mol % AIM in the polymer matrix is kept between 0.1 and 1. The degree of crosslinking is between 1 and 2 mol % crosslinker on the basis of all co-monomers. Both these variables influence the electrochemical performance. If the Fc units in the hydrogel are not well solvated, the redox properties are more similar to those of insoluble ferrocene materials. This can occur if the ferrocene content is greater than 0.5 to 1 mol % of the matrix, or if the crosslinking density is greater than 1.5 to 2 mol %. If the ferrocene content is less than 0.1 to 0.2 mol %, there will not be enough ferrocene density to render a strong redox signal. If the crosslinking density is less than 0.8 to 1 mol %, the hydrogel will lack physical integrity and can detach from the substrate or undergo gradual dissolution.

In some instances, the mol % AIM in the polymer matrix is kept between 0.1 and 1.5. The degree of crosslinking is between 1-2 mol % crosslinker on the basis of all co-monomers. The resulting hydrogel exhibits good structural integrity and bond strength with the surface of the electrode via a non-covalent attachment. In some instances, this type of embodiment survives gamma irradiation treatment as may be required to sterilize the sensor for use in the biotechnology, pharmaceutical, and food processing industries.

In other embodiments, hydrophilic derivatives of ferrocene monomers may be used so that there is good solvation with greater than 1 mol % ferrocene in the polymer chain. Similarly, bulky Fc monomers can be used to prevent aggregation and aid in solvation.

Thus, in some embodiments the materials for making an IE provided by the invention comprise an AIM covalently linked to a hydrophilic polymer matrix (or to a monomer that can be used in the formation of such a matrix). When the matrix is cross-linked as described herein, it is referred to as a "hydrogel." Thus, materials provided by the invention include "AIM polymers", "AIM hydrogels", "AIM monomers", and various other monomers for preparing them. In one embodiment, the AIM hydrogel of the invention comprises ferrocene in a cross-linked hydrophilic polymer. In one embodiment, the AIM hydrogel is formed by copolymerization of vinylferrocene with one or more hydrophilic co-monomers, at least one of which co-monomers is bi- or multi-functional. Bi- or multifunctional co-monomers are capable of forming crosslinks upon polymerization, and are referred to herein as crosslinkers. Copolymerization of these components yields a hydrogel that provides an IE that exhibits a pH-insensitive signal under SWV operating conditions. This signal is then used in conjunction with a pH-dependent signal from an ASM WE as described above to generate a signal corresponding to analyte concentration, in one embodiment pH, in accordance with methods described herein.

In the preferred embodiment, the AIM hydrogel comprises a polymer formed from radical polymerization of N,N-dimethylacrylamide (97-99 mol %), poly(ethyleneglycol)diacrylate (1-2 mol %), and vinylferrocene (0.1-1.5 mol %).

In another embodiment, an Fc monomer could be used as a linear homopolymer with no crosslinking. As mentioned above, vinylferrocene is not sufficiently hydrophilic to be a preferred embodiment. However, Fc derivatives, such as those illustrated in structure Fc-II of Table 1 below, can be prepared in accordance with the invention with appropriate hydrophilic linkers between the Fc and the polymerizable group to increase overall hydrophilicity.

In another embodiment, a multifunctional Fc monomer containing two or more polymerizable groups, such as that illustrated in structure Fc-III of Table 1, below, could be used alone to provide a cross-linked homopolymer. In this case each repeat unit of the polymer would contain an Fc group, which results in an exceptionally high Fc functionality but can provide increased pH sensitivity for some applications. By introducing a hydrophilic co-monomer as linker, as in some embodiments of the invention, the Fc functionality is "diluted" and the resulting copolymer exhibits enhanced hydrophilicity.

In another embodiment, the AIM hydrogel is a linear copolymer comprising an AIM monomer and one or more mono-functional co-monomers. This is illustrated in structures Linear Polymer 1 and 2 in Table 3 below. Co-monomers can be hydrophilic, with pendant groups that aid in solvation of the AIM, as illustrated in Linear Polymer 2. Linear polymers must be sufficiently large (greater than 50-100 monomer units per chain) to prevent leaching from the electrode substrate on which the AIM hydrogel is deposited.

In another embodiment, the AIM hydrogel comprises an AIM molecule physically entrapped in a cross-linked polymer matrix. Suitable AIM molecules may be linear polymers of length 50-10,000 units, such as illustrated in structure Linear Polymer 1, or may be oligomers or dendrimers, as illustrated in structures shown in Table 4 below. Such a structure, called an interpenetrating network (IPN), would enable an arbitrary AIM molecule to be entrapped in a cross-linked polymer without the need for polymerizable groups on the AIM. Components of IPNs are generally not covalently bonded to one another.

For the present embodiment, the preferred polymerizable groups are those which undergo radical polymerization including vinyl, acrylamide, methacrylamide, acrylate, and methacrylate groups. These have the advantage of resulting in an alkyl polymer chain which is chemically robust and stable to hydrolysis. The molecules themselves can include hydrophilic groups such as alcohols or ethylene glycol units, or AIM moieties including ferrocene.

In another embodiment, the polymerizable groups comprise those that react through amide or ester bond formation, including monomers containing both reactive carbonyls (such as acid chlorides) and nucleophiles (such as alcohol or amine groups). These result in polyester or polyamide polymer chains.

In another embodiment, the hydrogel comprises a non-covalently cross-linked hydrogel, also known as a supramolecular hydrogel, usually made up of amphiphilic colloidal components. This embodiment is considered to be less favored because supramolecular hydrogels are in general less robust to dissolution by heat and solvents.

TABLE 1

Ferrocene-containing monomers

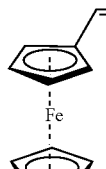

Fc-I

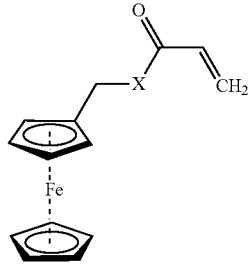

Fc-II

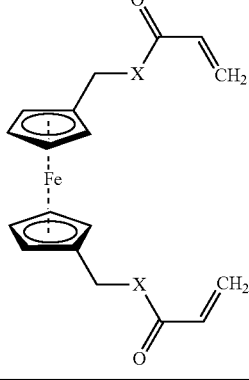

Fc-III

Typical ferrocene-containing monomers are shown in Table 1. One example used in a preferred embodiment is vinylferrocene (Fc-I), in which the polymerizable group is directly linked to the ferrocene aromatic ring. Another example, illustrated in structure Fc-II, features an acrylate (X=oxygen) or acrylamide (X=nitrogen) polymerizable group connected through a methylene linker. The linker can be $C_nH_{2n}$, where n can be 1-6. The linker can also include hydrophilic groups such as ethylene glycol units. The alkene portion of the polymerizable group can be either acryl (shown) or methacryl, in which a methyl group is attached to the carbon in the alpha position relative to the carbonyl group. These different derivatives may be desirable due to differences in polymerization rate and resistance to hydrolysis. Hydrolysis of the pendant AIM moiety on the polymer chain contributes to signal decay. Another type of AIM monomer is one containing two or more polymerizable groups, illustrated in structure Fc-III above. Such structures provide crosslinking in a polymer and could be used either alone or as a copolymer with other monomers. AIM polymers and AIM hydrogels can be based on any hydrophilic polymer matrix. Vinyl polymers are particularly suited because of the wide variety of properties obtainable by controlling the identity and formulation of monomers, co-monomers, and crosslinkers. Crosslinking provides an advantage in that the polymer can be polymerized in-situ, forming a robust network that physically attaches to the substrate, optionally penetrating substrates with certain degrees of porosity. Various levels of anionic, cationic, or zwitterionic character can be introduced into the hydrogel by incorporating monomers with those attributes. Suitable monomers include those listed below in Table 2 and Table 3. While ferrocene hydrogels are referenced below, other AIMs, such as organometallic, ionic salts and redox active organic species, can be formed into hydrogels using these monomers as well.

For example, viologen polymers are well-known as robust, hydrophilic, polyelectrolyte structures with two reversible redox peaks (Naoki et al. "Polyviologen Hydrogel with High-Rate Capability for Anodes toward an Aqueous Electrolyte-Type and Organic-Based Rechargeable Device."*ACS Applied Materials & Interfaces* 5.4 (2013): 1355-1361.) Metal salts traditionally used as redox markers, such as hexacyanoferrate, can also be incorporated into polymers in accordance with the invention by replacing one of the ligands with a polymerizable group.

TABLE 2

Radical-initiated monomers

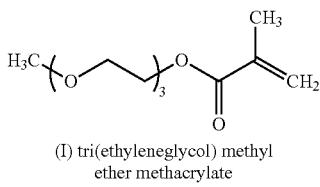

(I) tri(ethyleneglycol) methyl ether methacrylate

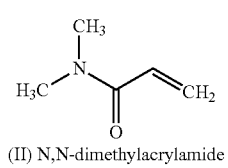

(II) N,N-dimethylacrylamide

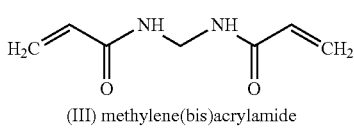

(III) methylene(bis)acrylamide

TABLE 2-continued

Radical-initiated monomers

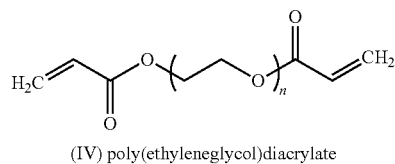

(IV) poly(ethyleneglycol)diacrylate

Typical radical-initiated monomers are shown in Table 2. Structures I and II are monomers known to be amphiphilic, capable of solvating hydrophobic molecules and also conferring the hydrophilicity of hydrogels. These structures contain an alkene group which participates in radical chain polymerization, resulting in an alkyl polymer chain with the pendant group shown. The pendant group can be chosen to impart hydrophilicity to the polymer.

Structures III and IV are bifunctional monomers used for crosslinking in a hydrogel. In structure IV, the spacer group can contain from 1 to 10 ethylene glycol units in the preferred embodiment, or from 20 to 1000 ethylene glycol units in other embodiments. The longer spacers can influence the swelling of the cross-linked hydrogel, depending on the bulk properties of the poly(ethylene glycol) chain used.

TABLE 3

Ionic monomers

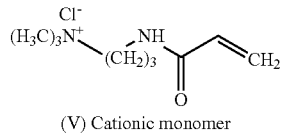

(V) Cationic monomer
(3-acrylamidopropyl)trimethyl-
ammonium chloride

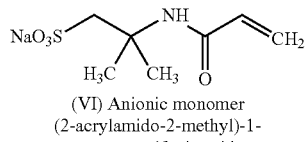

(VI) Anionic monomer
(2-acrylamido-2-methyl)-1-
propanesulfonic acid

Two exemplary ionic monomers are shown in Table 3. These monomers can increase hydrophilicity of AIM polymers beyond that achievable with nonionic monomers.

A wide range of polymer/hydrogel properties is obtainable by varying the choice of co-monomers and/or cross-linking agents, the ratio of these components, and the total solids content of the hydrogel. Solids content refers to the proportion of the gel taken up by the polymer matrix as compared to water. Typical hydrogels contain between 1 and 10% solids, and this can depend largely on the capacity of the material to absorb water and swell. This swelling itself is highly dependent on the degree of crosslinking. In some embodiments of the present invention, the AIM polymer or AIM hydrogel incorporates vinylferrocene (or other suitable ferrocene derivative or other AIM-linked monomer or polymer, or admixed preparations of an AIM and a monomer(s)) throughout the three-dimensional polymer structure, enabling a much larger effective population of the AIM than previously achievable without exceeding the threshold density of ferrocene (or other AIM) groups that results in a narrower than desired pH-insensitivity range.

Representative polymers prepared using the methods of the invention are shown in Table 4 and Table 5. These include linear polymers containing vinylferrocene and co-monomer N,N-dimethylacrylamide (II) or the more hydrophilic triethyleneglycol methyl ether methacrylate (I), or diethyleneglycol methyl ether methacrylate (analogous to I, except n=2), and ferrocene-containing hydrogels cross-linked with poly(ethyleneglycol)diacrylate (IV) or methylene(bis)acrylamide (III). In Table 4 and Table 5, x, y and z refer to the stoichiometric ratio of each monomer. For example, the ratio of x:y corresponds to the degree of ferrocene (or other AIM) substitution of the host polymer (for example the 0.1 to 1 mol % ferrocene discussed above).

TABLE 4

Linear polymers

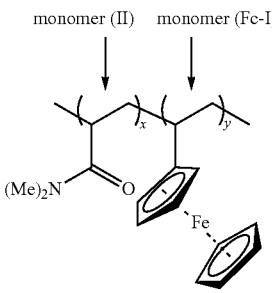

Linear polymer 1

TABLE 4-continued

Linear polymers

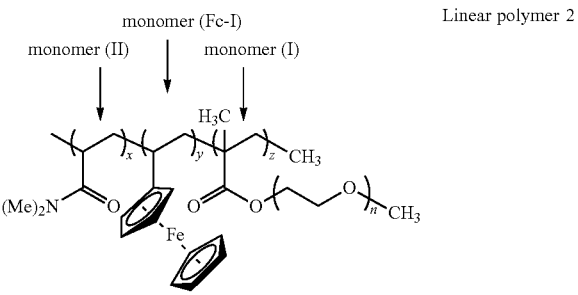

Linear polymer 2

Table 4 shows examples of linear polymers incorporating Fc as the AIM. The values x, y, and z indicate the stoichiometric ratios of the monomer units, which are distributed randomly throughout the polymer. In preferred embodiments illustrated with Linear Polymer 1, ratios of x and y can be 100:1 to 1000:1. In preferred embodiments illustrated with Linear Polymer 2, ratios of x, y, and z can be 90:1:10, 85:1:15, 80:1:20, 900:1:100, 800:1:200, and 0:1:100. In other embodiments, a block copolymer can be used such that the exact placement and distribution of groups of monomer chains are known.

Linear polymers 1 and 2 illustrate the methods and materials relating to the incorporation of Fc (for illustrative purposes; any AIM can be used) functionality into a hydrophilic polymer. The use of three co-monomers in Linear polymer 2 offers control of the degree of hydrophilicity and other physical properties. However, both linear polymers dissolve in water over time; hence, crosslinking can be used in accordance with the invention to slow or eliminate dissolution.

Cross-linked polymers 1 and 2 incorporate crosslinkers III and IV, respectively, as shown in Table 5, wherein the crosslinkers are highlighted in bold.

TABLE 5

Cross-linked polymers

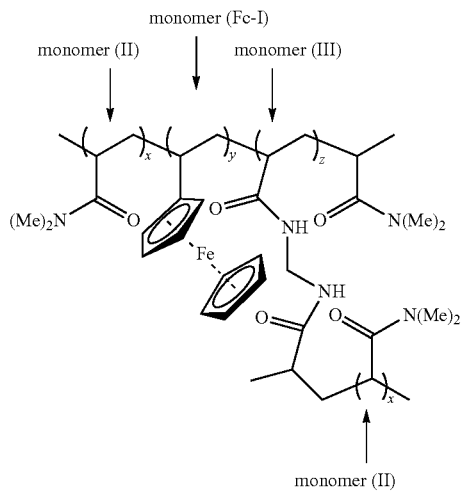

Crosslinked polymer 1

TABLE 5-continued

Cross-linked polymers

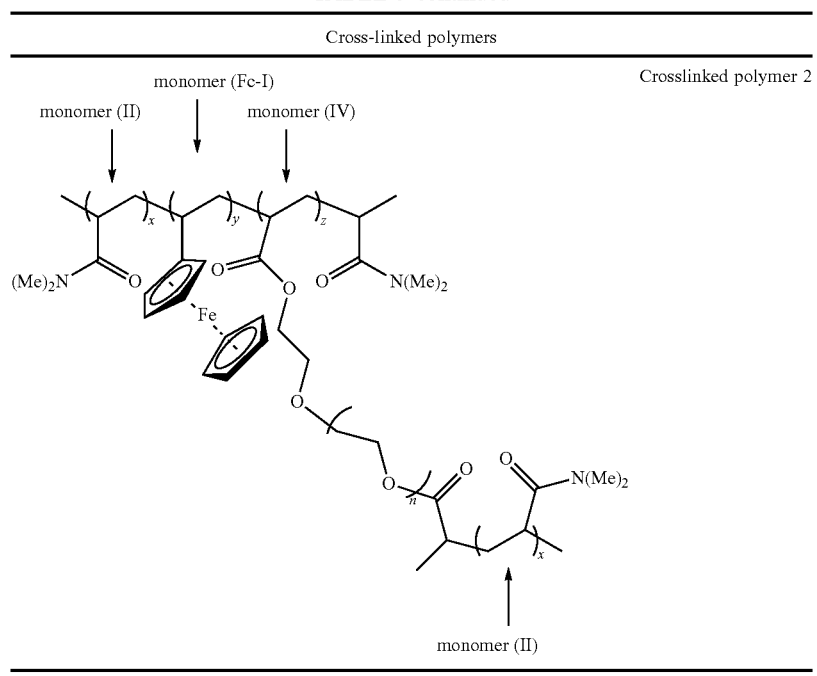

Table 5 shows examples of cross-linked polymers incorporating Fc as the AIM. The values x, y, and z indicate the stoichiometric ratios of the monomer units, which are distributed randomly throughout the polymer. For cross-linked polymer 2, it may be preferred to modify the bifunctional crosslinker such that it contains amide, rather than ester, linkages which are more robust to hydrolysis. In preferred embodiments for cross-linked polymers, such as those shown, the ratios of x, y, and z may be 1000:1:5 to 1000:1:20; 1000:10:5 to 1000:10:20. In other embodiments the polymer is comprised solely of AIM monomer and crosslinker monomer, with ratios of 0:1:1000 to 0:20:1000.

In some embodiments, polyvinylalcohol is functionalized with ferrocene and a linear polymer of the instant invention (e.g., a linear polymer which includes acetyl groups, ferrocene and hydroxyl groups) that is either thermally cross-linked, chemically cross-linked, or cross-linked via radiation. For example, in one instance the crosslinkers are selected from the group consisting of maleic anhydride, maleic acid, glutaraldegyde, diisocyanate, divinyl ether, periodate, or any generic dialdehyde, as disclosed in http://ntrs.nasa.gov/archive/nasa/casi.ntrs.nasa.gov/19790012957.pdf, which disclosure is incorporated herein in its entirety. In some instances, PVA is functionalized with a ferrocene derivative having either a long side chain, or a shorter side chain and/or an electron withdrawing or electron donating group which is favorable in adjusting the peak potential to a more positive or more negative potential, depending upon the application. In some embodiments, certain ferrocene derivatives are selected because they are more robust and resistant to scan-dependent decay, as disclosed in http://www.ncbi.nlm.nih.gov/pmc/articles/PMC2975373/table/T1/, which is incorporated herein in its entirety.

Those of skill in the art will appreciate that the present invention provides monomers, polymers, and hydrogels useful in making WEs, as well as WEs formed using the same, which differ from the AIM materials described above only in that the AIM is replaced by an ASM. Thus, the electrochemically active component of hydrogels of the invention can include either analyte insensitive materials, analyte sensitive materials, or both. For example, vinylanthracene or 2-acrylamido-anthraquinone (shown below in Table 6) can be incorporated into hydrogel matrices described above to form an ASM hydrogel of the invention. Alternatively, both ASM- and AIM-vinyl monomers may be used as co-monomers in the same hydrogel that exhibits both analyte-sensitive and analyte-insensitive responses.

TABLE 6

Electrochemically active components

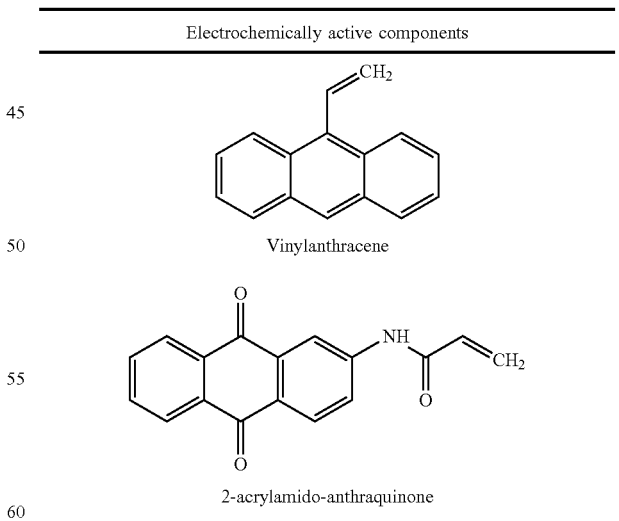

Vinylanthracene 2-acrylamido-anthraquinone

In various embodiments of the electrodes, sensors, and devices of the invention, a polyacrylamide ferrocene conjugate and a polyacrylamide anthraquinone conjugate are used as an AIM and ASM respectively. Such embodiments include two linear polymers or a copolymer where both the ASM and AIM are incorporated in the polymer matrix as co-monomers resulting in a random copolymer of the desired composition. Such embodiments also include those in which the WE and IE are on separate substrates.

In some embodiments, an AIM such as a ferrocene derivative that is already in the form of an oligomer, polymer, or dendrimer, is used to prepare an AIM hydrogel in which the AIM is not covalently attached to the hydrogel but rather retained therein by physical entrapment. Effective physical entrapment requires that the effective network density of the hydrogel be sufficiently high to minimize diffusive loss of the ferrocene derivative (or other AIM) component. Monomeric AIMs are generally not suitable for physical entrapment as the high network density needed to retain them effectively is contrary to the requirement of a highly swollen hydrogel. The illustrative ferrocene materials shown in Table 7 are suitable for such immobilization. Alternate hydrophilic scaffolds, including those based on sol-gel chemistry (see PCT Pub. No. 2012/018632, incorporated herein by reference), can be used to form IPNs to immobilize AIM polymers or AIM hydrogels (or corresponding materials with ASMs for preparation of WEs of the invention) with average molecular weights sufficiently high compared to the effective pore size of the scaffold to provide adequate immobilization.

TABLE 7

Ferrocene materials for use in forming IPNs
Ferrocene materials that can be entrapped in hydrogel at electrode surface.

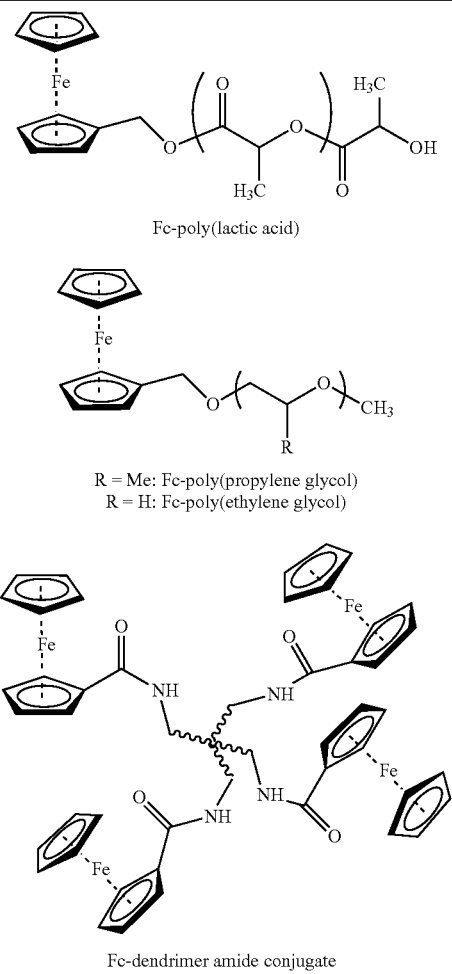

Fc-poly(lactic acid)

R = Me: Fc-poly(propylene glycol)
R = H: Fc-poly(ethylene glycol)

Fc-dendrimer amide conjugate

Ferrocene (or other AIM) polymers can also be blended into other polymer matrices to yield AIM polymers and AIM hydrogels of the invention. Such matrices are selected to impart certain attributes, e.g. thermal or chemical resistance, that exceed the performance envelop of hydrogels. Polyvinylidenefluoride (PVDF), epoxy, electropolymerized polypyrrole, and various conductive ink formulations are exemplary materials that may be used for this purpose. These and other polymers are sometimes employed to meet the mechanical, dielectric, or physicochemical requirements of application-specific sensors.

Electrode Design

The invention provides robust electrodes without covalent attachment of the AIM to the substrate or the ASM to its substrate, which may be the same or different. In some electrodes of the invention, the AIM hydrogel is secured to the substrate surface by non-covalent means. The invention provides substrates that enhance such attachment, having the appropriate level of surface texture, porosity, and/or three-dimensional tortuosity to ensure secure immobilization. These features can improve attachment and/or containment of the AIM hydrogel (or ASM hydrogel) without affecting the AIM's interaction with the analyte, in part benefitting from the highly permeable nature of the swollen hydrogel. They also provide protection against physical damage associated with contact, abrasion, or detachment that might otherwise result from repeated swelling and shrinking of the AIM hydrogel, compared with the same material deposited on a smooth surface such as glassy carbon, or other metallic and non-metallic surfaces. In effect, the mechanical properties of the textured or porous substrate overcome the inherent fragility of AIM hydrogel to deliver high structural integrity.

Any conductive substrate can be used as an electrode for the support, immobilization, and protection of AIM polymers and AIM hydrogels (and ASM polymers and ASM hydrogels) of the invention. These can include carbon allotropes such as carbon fiber, porous graphite, macroporous carbon, mesoporous carbon, microporous carbon, nanoporous carbon, carbon nanofibers (made by carbon-coating on materials such as nanoporous alumina) and their composites; and nanotubes and their composite. Metals can include nanoporous gold, platinum, and silver. Screen-printed electrodes can have a variety of surface coatings with desired roughness including mesoporous carbon, carbon nanofibers, carbon nanotubes, graphene, or carbon ink imprinted with micro- or nano-scale features such as channels or pores. Porous conductive substrates benefit further from very short signal pathways, thereby increasing signal capture efficiency.

Certain conductive polymers can be used as an electrode substrate and coated with AIM hydrogel. Engineering polymer composites that contain sufficient quantities of carbon allotrope or metal particles to render them conductive can be used as supports for the AIM hydrogel. Suitable polymers for such composites include epoxy, polysulfone, polyethersulfone, polyphenylenesulfide, polypyrrole, polyvinylidenefluoride, other fluoropolymers or copolymers, and various vinyl polymers such as PVC, polystyrene, polymethylmethacrylate, and their derivatives and copolymers, cellulosic polymers, and silicone polymers.

Figure 8:
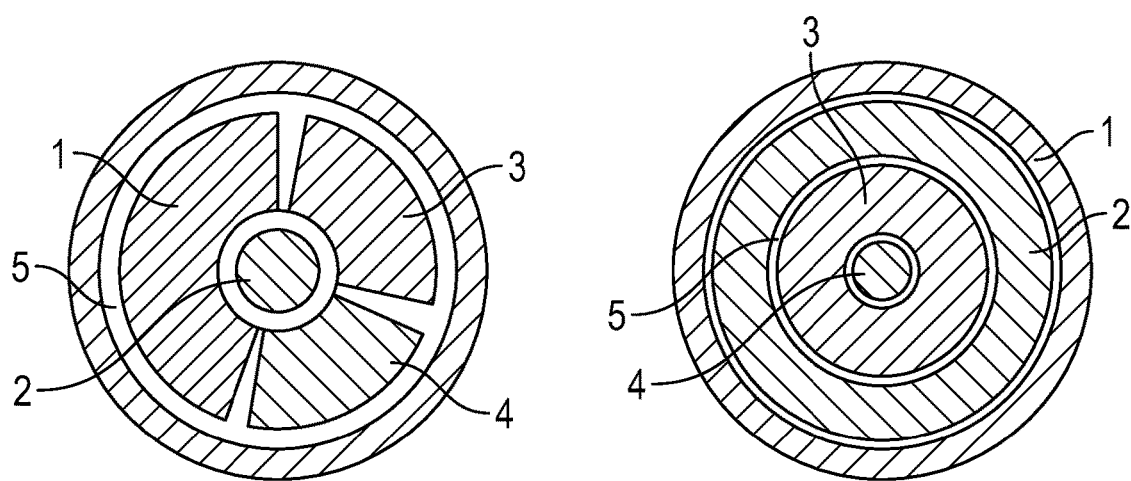
FIG. 8 shows various electrode configurations of sensors (devices) of the invention.

Electrodes of this invention can be made using rigid substrates such as various carbon composites, or on flexible conductive substrates (e.g. woven or nonwoven carbon fabric), or a nonconductive support film such as polyester, polyimide, polyolefin, etc. that has been rendered conductive with a conductive coating (such as carbon ink, indium tin oxide, silver, etc.). The materials of the present invention may be formed in various geometric patterns, complemented by the CE and PRE in close proximity. For example, the electrodes may be arranged as concentric rings, segments, and arrays, as shown in FIG. 8. Conductive coatings and electrodes derived therefrom allow sensors to be built in a wide range of form factors and dimensions.

With continued reference to FIG. 8, in some embodiments electrode components 1, 3 and 4 of a solid state sensor are arranged as sections in a single concentric ring surrounding a central electrode 2. For example, in one embodiment a sensing surface of a solid state sensor comprises a single concentric ring having a plurality of electrode segments, namely an ASM-containing WE 1, a pseudo reference electrode 3, and a counter electrode 4, wherein the individual electrode segments are radially arranged around a centrally located AIM-containing IE 2. The sensing surface further comprises a nonconductive material 5 that is interposedly positioned between the plurality of electrodes. In some instances, the exposed surface areas of the various electrode segments are selected so as to produce a desired signal relative to one or more other electrode segments.

In some instances, sensor materials or composites are formed into micro-hemispheres with characteristic radii on the order of 25 micrometers or less. Sensors of these dimensions generate very low signals, but their reduced double layer capacitance also shortens the response time. (see J. Wang, *Analytical Chemistry*, $3^{rd}$ ed., 2006, John Wiley). Sensor arrays can be constructed for use in miniaturized or microelectrodes with viable signal levels for practical applications.

In some instances, electrode components 1, 2 and 3 are provided as individual concentric rings surrounding a centrally located electrode component 4. Non-conductive material 5 is interposedly positioned between each of electrodes 1, 2, 3 and 4 to isolate the respective signals of each electrode component. In some instances, the position of a sensor components is selected based upon the desired, exposed surface area of the sensor component relative to one or more other electrode rings. In some instances, each concentric electrode ring comprises an equal width. In some instances, one or more concentric electrode rings comprises a unique width relative to one or more other electrode rings.

Conductive substrates may be further supported using robust supporting materials such as ceramic, glass, or glass fiber-reinforced composites commonly used for printed circuit boards. These materials provide well-established connectivity options for transferring signals from the sensing elements to the electronic circuitry. Various packaging options (such as multilayer printed circuit boards, plate-through contacts etc.) offer increased packaging density, reliability, and functionality of sensors and devices.

The AIM hydrogel and ASM hydrogel may be applied to substrates as a coating. In various embodiments, however, the AIM hydrogel or ASM hydrogel is formed in-situ to obtain cross-linked structures. When applied as a coating, the AIM polymer (or ASM polymer) must be sufficiently soluble in a solvent or solvent mixture to prepare the coating solution, but be sufficiently insoluble in the intended analyte—usually water—that it remains on the electrode surface for the lifetime of the sensor. This often limits the hydrophilicity of candidate linear AIM (or ASM) polymers. Crosslinking the AIM (or ASM) polymer obviates this trade-off, as even low degrees of crosslinking render even highly hydrophilic polymers insoluble.

However, because of this insolubility, cross-linked polymers cannot be applied as a solution and must be prepared in-situ. This involves applying a solution of monomers and initiator on the substrate, and then initiating the polymerization process. The monomers can thus penetrate into pores of the substrate before polymerization and crosslinking. This ensures that even without covalent linking to the surface, the polymer will have excellent adhesion to the substrate and conform to any surface features and internal structures. Crosslinking is especially beneficial to impart dimensional stability, and to retain lower molecular weight fractions of the AIM (or ASM) hydrogel, which contribute to extending the functional life of the AIM sensor (IE) or ASM sensor (WE). Example 1, below, illustrates this aspect of the invention by demonstrating how to make a ferrocene-containing electrode (IE) of the invention by producing a cross-linked hydrogel on an electrode surface in which the substrate is a carbon substrate.

The AIM and ASM hydrogels of the present invention exhibit good wet-dry reversibility, retaining their physical integrity upon drying, and rapidly restoring their redox activity and electrode potential upon rewetting.

Square wave voltammetry (SWV) methods are used to generate signals from sensor components of the present invention. Signals generated by the WE and the IE can be monitored simultaneously or at different intervals. In the current context, the terms "sweep" and "scan" are used interchangeably. In embodiments where both the ASM and the AIM are located on the same substrate, a square-wave potential sweep is applied to elicit separate but contemporaneous responses from the ASM and the AIM. The same scan parameters (such as the range of voltage sweep, pedestal height, and interval between scans, also referred to as dwell time) are applied to both electrodes.

In other embodiments where the ASM and the AIM are located separately on discrete, electrically independent electrodes, and in accordance with important new methods provided by the invention, two separate square-ware potential sweeps with different scan parameters can be applied to the electrodes. Sampling the WE and IE separately offers several benefits. First, signal quality can be individually optimized for the ASM and for the AIM. Second, the IE can be sampled less frequently than the WE some AIMs are designed to remain unchanged in different analytes. Thus, the IE only needs to be sampled to reconfirm stasis when a change in analyte takes place or is expected. Time that is not spent on sampling the IE can be used to resume monitoring of the WE, in effect shortening the WE dwell time and resulting in a more responsive pH measurement system. Third, less frequent sampling of the IE allows certain AIM materials to be employed that exhibit good accuracy and broad pH-insensitivity ranges but are susceptible to signal loss as a result of repetitive electrochemical excitation.

Figure 11:
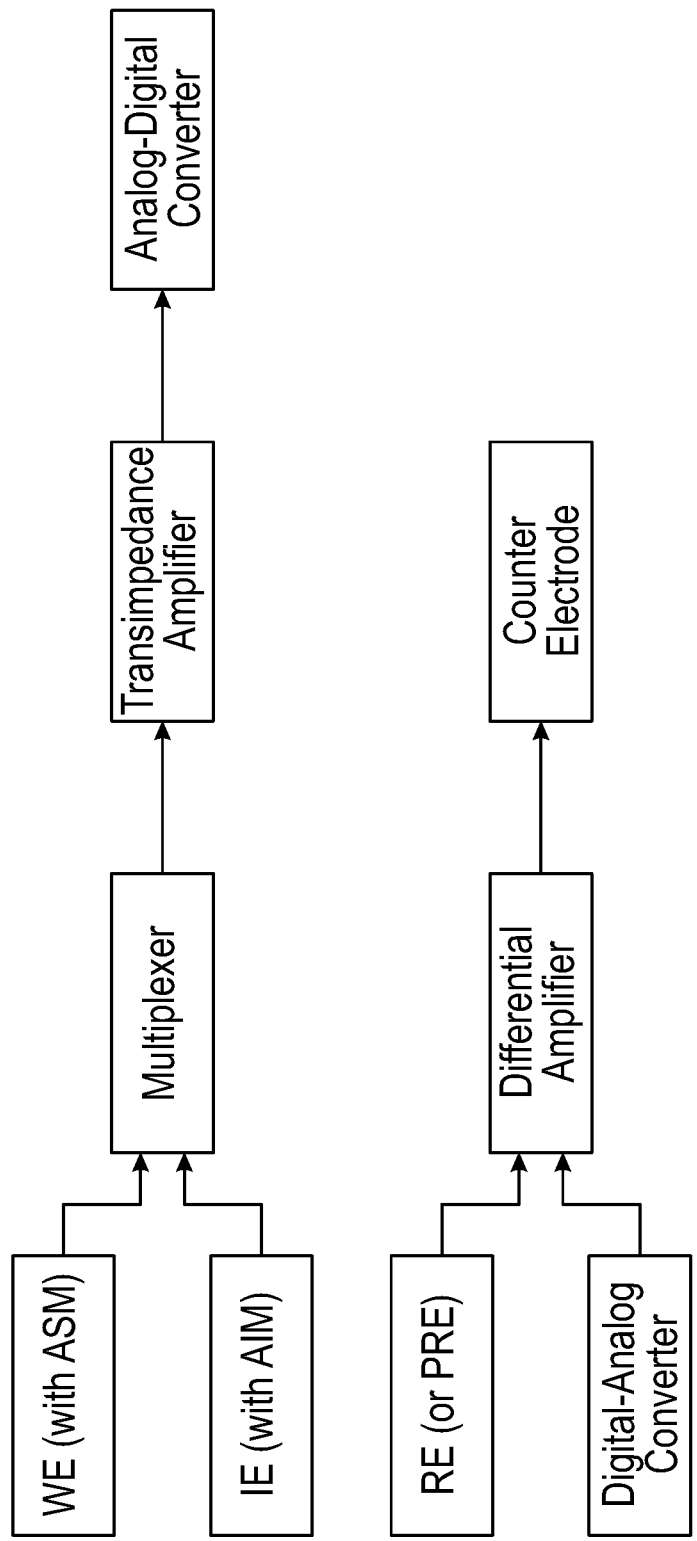
FIG. 11 is a diagram illustrating the operation of SWV electronics of sensors of the invention.

In one embodiment, SWV electronics of sensors of the invention are configured to multiplex between the inputs from the WE and the IE. The WE and IE inputs are electrically equivalent and are in common with the reference electrode/pseudo reference electrode (RE/PRE) and CE circuits. The operation of this system is illustrated in FIG. 11.

The differentiating feature of the potentiostat circuitry (Blocks 1 to 9) is a multiplexer (3), used to select either the ASM or AIM electrodes. The transimpedance amplifier (4), analog-digital converter (ADC) (5), Reference Electrode (6), digital-analog converter (DAC) for generating the square wave excitation (7), and Difference Amplifier (8) that drives the Counter Electrode (9) are common to both the WE the IE.

The SWV operating parameters, including voltage scan (or sweep) range, pedestal height, equilibration time, and dwell time (i.e. rest time between sequential voltage scans), are independently adjustable for the WE and IE. In one embodiment, the same SWV circuit is used to monitor the WE and IE sequentially.

Figure 12:
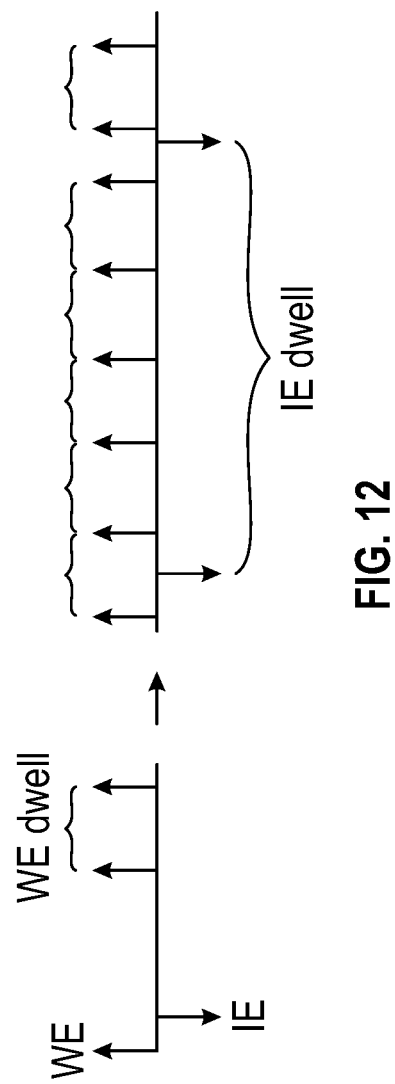
FIG. 12 is a diagram illustrating overall time sequence of WE and IE scan.

The overall time sequence of WE and IE scan is shown in FIG. 12. Arrows represent grouping of scans, or repetitions, occurring at regular intervals set at independent dwell times.

The scan parameters are optimized for each electrode. Statistics, i.e. peak potential averages and standard deviations of a series of repetitions of scans, can be kept separately for the WE and IE so that the results from these electrodes can be independently analyzed.

Operating parameters for the SWV for the WE and IE of the present invention, including typical ranges and preferred values, are shown in Table 8.

TABLE 8

Operating parameters for SWV for WE and IE

| | | WE (with ASM) | | IE (with AIM) | |
|---|---|---|---|---|---|
| Parameter | Mode | Range | Preferred | Range | Preferred |
| Scan Rate | | 30 to 120 mV/s | 60 mV/s | 30 to 120 mV/s | 60 mV/s |
| Pedestal Height | | 1 to 150 mV | 100 mV | 1 to 150 mV | 25 mV |
| Step Height | Seek | 1 to 10 mV | 8 mV | 1 to 10 mV | 2 mV |
| | Tracking | | 2 mV | | 2 mV |
| Scan Width | Seek | −1000 mV to +100 mV | | −100 mV to +800 mV | −100 mV to +500 mV |
| | Tracking | Peak +/− 250 mV | | Peak +/− 200 mV | |
| Dwell | | 0 to 3600 s | 30 s | 0 to 3600 s | 1200 s |

A special feature of the SWV technique of the invention is the implementation of two operating modes. First, a "seek" mode is used at the beginning of each voltage scan covering a relatively broad potential range in order to locate the peak potential of the ASM or AIM in the analyte. Second, a "tracking" mode is used with smaller voltage increments in order to locate the peak potential from the electrode at higher resolution. In the tracking mode, for example, the step height of 2 mV corresponds to a pH resolution of 0.03 pH units. This is sufficient for most pH analysis applications. It is possible to reduce the step height further to 1 mV (for a resolution of 0.015 pH unit), but doing so also increases the time needed to span the ±200 mV range. A narrower scan width is sufficient for the AIM peak potential is largely invariant.

The following procedure describes how the signals from the WE and the IE are used to derive the concentration of the analyte of interest, in this case the hydronium ion concentration expressed as pH.

Figure 13:
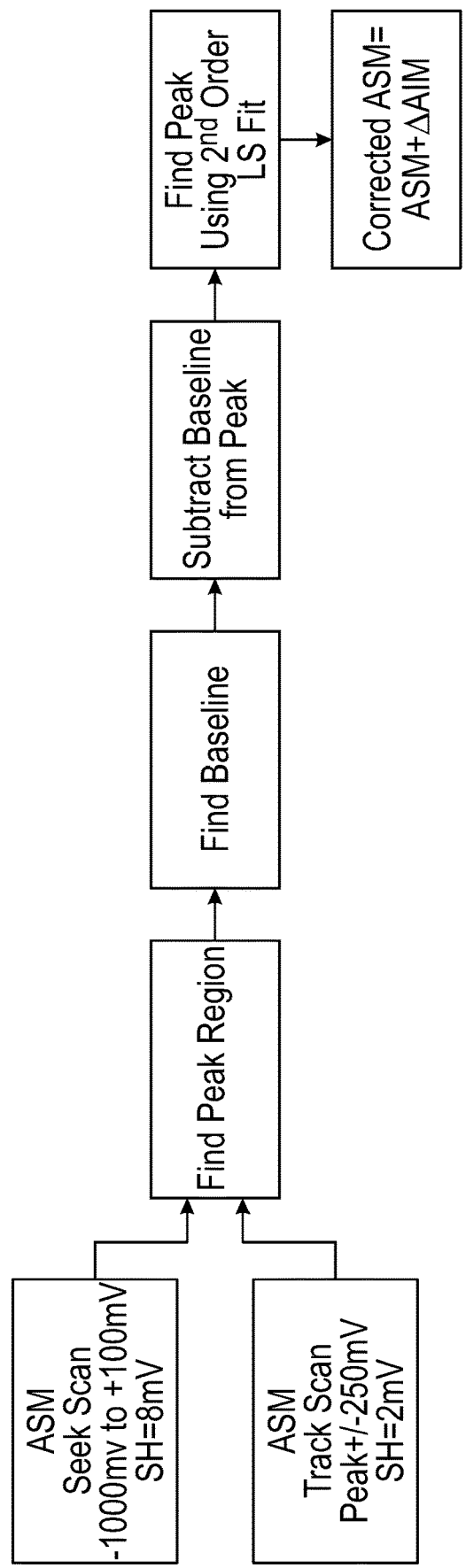
FIG. 13 is a diagram illustrating WE scan, baseline correct, peak pick, calculate ASM peak potential, and ASM correction.
Figure 14:
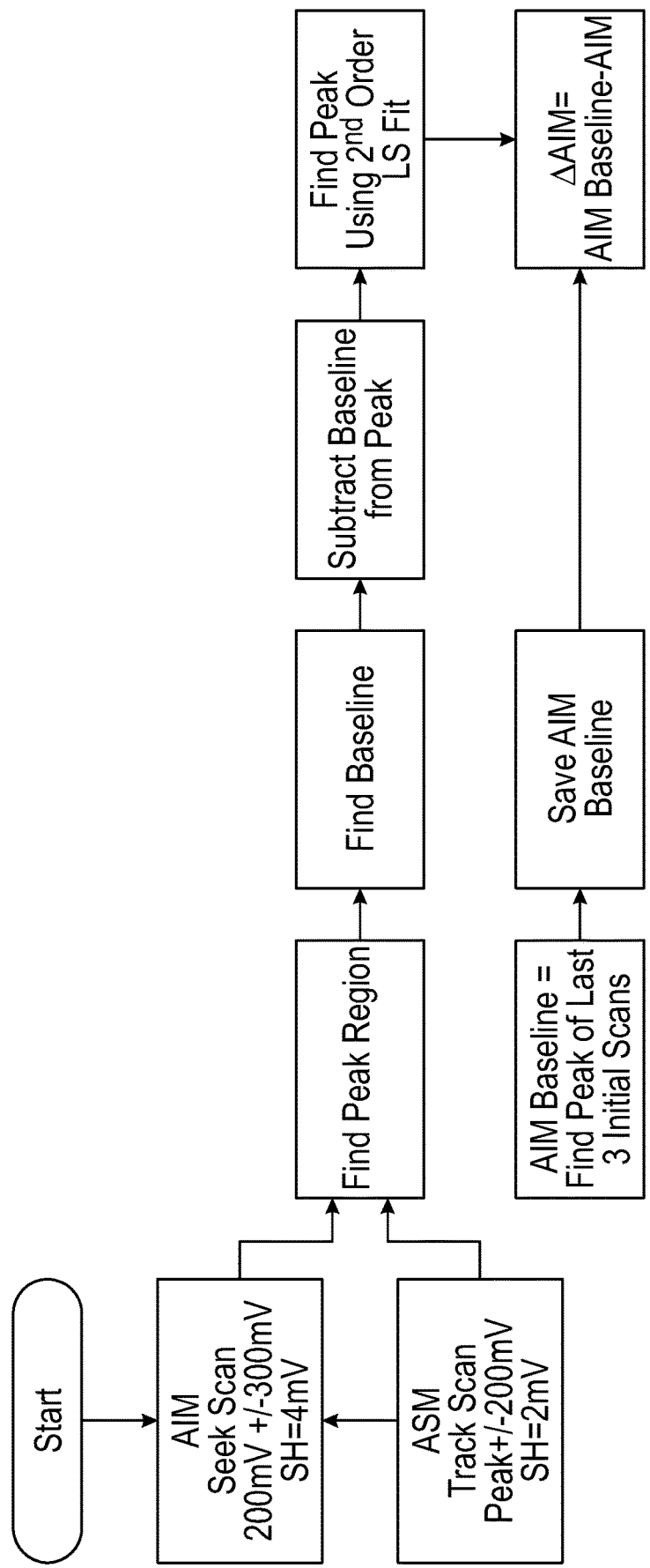
FIG. 14 is a diagram illustrating IE scan (baseline corrected, peak-picked) used to calculate AIM peak potential and ΔAIM.

As shown in FIGS. 13, 14 and Table 9, the start of the scan (1) begins with a wide SWV sweep of the WE at low resolution (2a) to Seek the Center of subsequent WE tracking scans (2b). The rate of the sweep is set by the step height (SH) of each voltage increment between the limits of the voltage range. Processing the SWV output to find the peak is summarized in steps 3 through 6. Just after the WE seek scan (2a), but before commencement of the WE tracking scans (2b), a wide SWV sweep of the IE (8a) seeks the center of subsequent IE tracking scans. The initial group of IE tracking scans are averaged to determine the AIM Baseline (9) and saved into non-volatile memory (10). The difference of the peaks (steps 3-6) of subsequent AIM tracking scans (8b) from the AIM Baseline is equal to ΔAIM (11). Because the AIM peak is invariant, ΔAIM reflects the drift of the RE or PRE. The ASM peak is corrected by ΔAIM (7), applied as a correction factor equivalent to the drift of the RE or PRE. The calibration table characterizes the average ASM response to standard buffers over a pH ranging (e.g. from pH 2 to pH 12) at several temperatures (e.g. from 5° C. to 50° C.). Entries for calibration table are made under controlled conditions, using a stable RE, such as Ag/AgCl or Calomel. From the calibration table, at the sensor temperature and the voltage equal to the Corrected ASM (7), the corresponding pH of the sample is determined (12).

TABLE 9

Calculate pH from predetermined calibration table (or function)

pH = f (Corrected ASM, Temperature)
-12-

Determining pH (or other analyte concentration) with a WE-IE pair of the invention can be performed as follows. A calibration table of the response of the ASM to pH buffers over the temperature range referenced to a standard Ag/AgCl or calomel reference electrode can be used, enabling correcting the ASM peak in response to the drift of the AIM. Another method is to prepare the calibration table directly from the difference between the ASM and AIM peak potentials to pH buffers over a given temperature range. These operations can be incorporated in the firmware of an analyte sensing device of the invention.

An analyte sensing device of the invention comprises a sensor assembly comprising at least one each of WE, IE, RE (CRE or PRE, but typically a PRE), and CE. These sensor components can be configured in various spatial arrangements, surface area ratios, planar or three-dimensional designs, in coaxial or non-coaxial geometries, or some combination thereof.

One desired configuration provided by the invention is a sensor assembly 12 mm in diameter. This geometry is similar to conventional glass electrodes, and thus compatible with instruments and installations. Sensing elements of the present invention can be co-located at the terminal planar surface of a probe 12 mm in diameter, or can be suitably recessed for protection, or can be organized in three dimensional space accessible to the analyte. The counter electrode can be one of the co-located components on the terminal surface, or be in the form of a collar or circular trace surrounding other sensing elements, as shown in FIG. 8.

Figure 9:
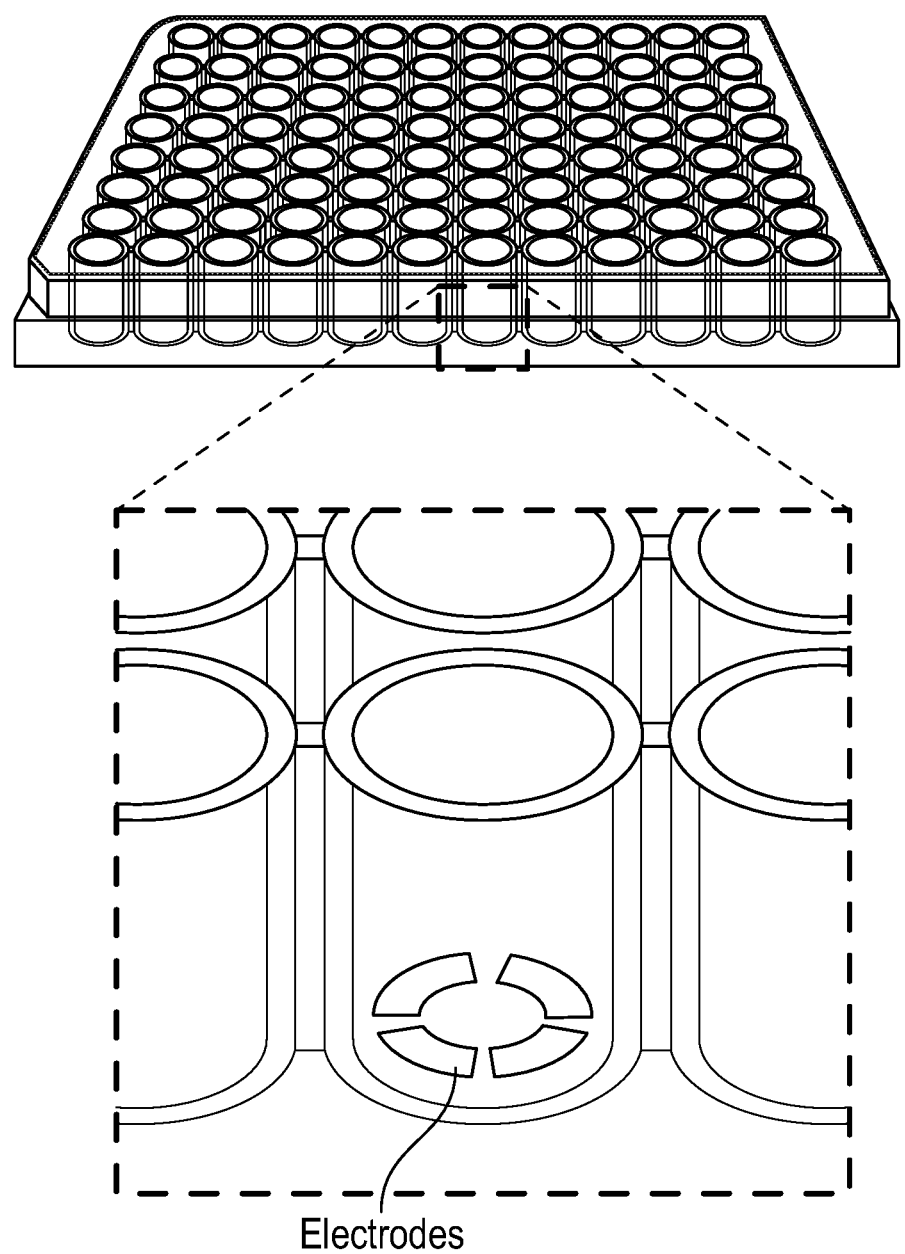
FIG. 9 shows a multiwall plate incorporating pH sensors of the invention.

Another embodiment provided by the invention is a multiwell or microwell plate in which there is an addressable sensor in the bottom and/or internal wall of every well, as shown in FIG. 9. The configuration of the electrodes is in some embodiments similar to the 12-mm probe designs above. The primary difference is in the size of the electrode surface, and in the electronics interface. In the case of a multiwell plate, the electrical connections to each electrode can be achieved through holes to the backside of the plate or by means of conductive traces. These connections are common in multiwell plate sensors for monitoring conductivity. In a typical configuration, a 96-well plate will contain 50-200 microliters of solution per well. The electrode surfaces at the bottom of each well will be on the order of 1-2 square millimeters; the diameter of the wells is about 1 cm. Various illustrative embodiments of sensor designs are shown in FIG. 8. In an alternate embodiment, electrodes may be incorporated into multiwell plates such that the analyte will contact all sensing elements to enable measurement. In certain embodiments, one or more electrodes are located on the walls of the sample cavity, leaving at least a portion if not all of the bottom transparent for optical analysis. Alternatively, printed electrodes located on a flexible film are particularly suited as components in flexible containers, tube sets, and other components for bioprocessing (including single-use or disposable components).

Figure 10:
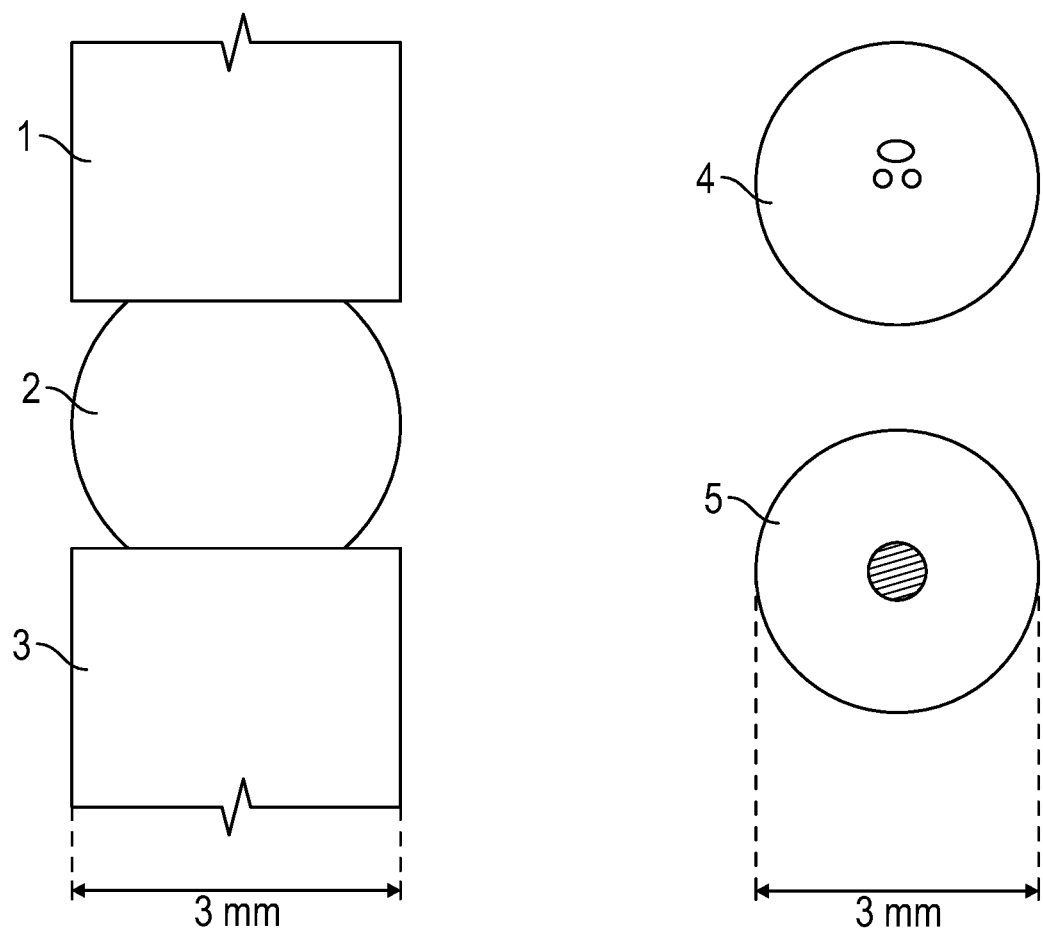
FIG. 10 shows details of a pH sensor designed to measure microliter samples, in accordance with a representative embodiment of the present invention.

Referring now to FIG. 10, the present invention is also applicable to pH measurements in very small analyte sample volume, in particular in accordance with PCT Pub. No. 2014/106066, incorporated herein by reference. This embodiment includes sensor assemblies and instruments derived therefrom for measurement of droplets of liquid on the order of microliters or sub-microliters. In this embodiment, the WE, IE, and PRE are all located in an area on the order of several square millimeters. In one embodiment, this is the WE/IE module. The proximity ensures the WE/IE module and RE will be in contact with the sample at the same time. The circuit is completed when a CE module, comprising a CE of similar dimensions, is brought into close proximity to the WE component. The gap formed between these sensor components is used to hold an analyte droplet by capillarity, bridging and wetting the electrode surfaces and completing the electrochemical circuit. There is current flow only when a sample droplet bridges the two parts of the sensory assembly.

Various aspects of the invention are also illustrated in the following examples.

EXAMPLES

Example 1: Ferrocene-Containing Electrode Produced by Forming a Cross-Linked Hydrogel on an Electrode Surface In this example, an AIM hydrogel of the invention is immobilized on (not covalently bound to) the electrode surface during the polymerization process used to form the hydrogel. After polymerization, the electrode is washed in water or water-solvent mixture to remove contaminants, unreacted monomers, and reaction byproducts. Excess hydrogel is removed from the electrode surface. The electrode is then mounted onto a housing where the hydrogel-containing surface is exposed to analyte solution. The conductive backside of the substrate is connected to a potentiostat. The AIM signal is obtained by applying a sweeping square wave potential with respect to a reference or pseudo-reference electrode to give a current peak. The current peak potential from the AIM is then used to correct drift in the reference electrode or as a reference for another working electrode (ASM).

In this example, the chemical structure of the AIM comprises ferrocene covalently linked to a hydrophilic, cross-linked polymer matrix of the invention. The electrode is produced by polymerizing a monomer mixture in the presence of a conductive substrate. A monomer solution comprising N,N-dimethylacrylamide (DMMA) with 5 wt % polyethyleneglycol (PEG) diacrylate and 1 wt % vinylferrocene was diluted in n-butanol to give a 25% solution. A heat-activated initiator (azobis isobutyronitrile, AIBN) was added to a concentration of 0.5% wt/vol. Electrode disks of carbon fiber were immersed in the mixture, which was then sonicated and sparged with argon to remove oxygen. The mixture was capped and heated at 60° C. for 24 h to produce a hydrogel of the invention. The electrodes were cut out of the gel and washed in fresh water for 2 days. Excess hydrogel was then removed from the electrode surface. The electrodes were stored in water until use.

Alternatively, the electrode is produced by polymerizing a monomer mixture in the presence of a conductive substrate, wherein, a monomer solution comprising N,N-dimethylacrylamide (DMMA) with 3 wt % N,N'-Methylene bis acrylamide and 3 wt % vinylferrocene was diluted in n-butanol to give a solution. A heat-activated initiator (e.g. azobis isobutyronitrile (AIBN)) was added to a concentration of 0.5% wt/vol. Electrode disks of carbon fiber were immersed in the mixture, which was then sonicated and sparged with argon to remove oxygen. The mixture was capped and heated at 75° C. Gelation took place between 20-60 min to produce a hydrogel of the invention. After 90 min, the electrodes were cut out of the gel and were allowed to swell in alcohol for 12-18 hours, after which the electrodes were washed in 1:1 alcohol:water mixture for 2 h and then DI water for 2 h. Excess hydrogel was then removed from the electrode surface. The electrodes were then stored in water until use.

Figure 3:
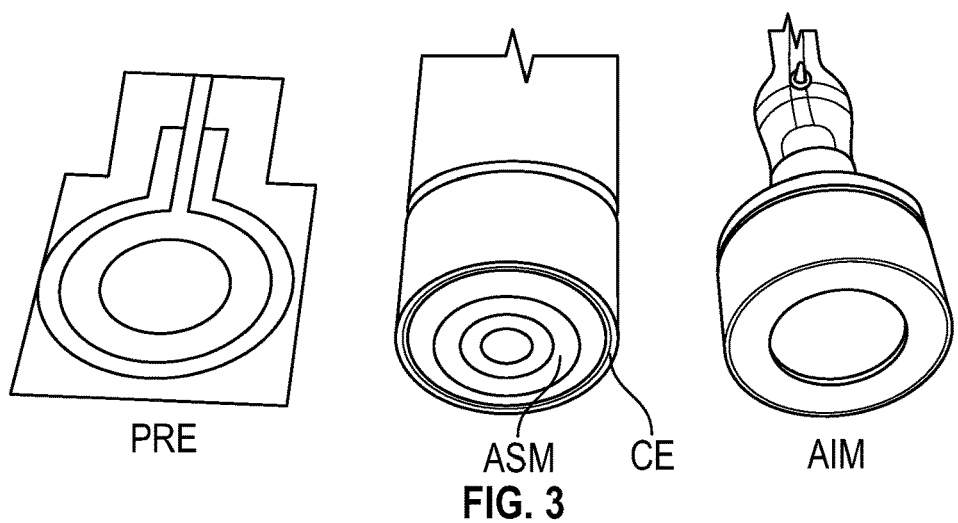
FIG. 3 shows the components for a calibration-free solid state pH sensor of the invention, as more specifically described in Example 1. The ASM is located on the WE, while the AIM is located on the IE. A carbon fiber composite material is used as substrate for both electrodes. The Counter Electrode (CE) in this embodiment is a metallic (e.g. stainless steel) ring surrounding the WE. All voltammetric measurements are made with respect to a pseudo-reference electrode (PRE) in this example.

Referring now to FIG. 3, four solid-state sensor components were deployed by simultaneous immersion in a given analyte solution. The IE was prepared by in-situ polymerization of a ferrocene-hydrogel onto a carbon fiber substrate. The WE utilized a polyvinyl alcohol anthraquinone (PVA-AQ) prepared as described US patent application publication no. 20130168609, incorporated herein by reference. Alternative chemistries for PVA-AQ, in accordance with the present invention, are provided in Example 4, below. The counter electrode CE was a stainless steel ring surrounding the WE. All voltammetric measurements were made with respect to a pseudo-reference electrode (PRE), which in this case was a screen-printed silver/silver chloride film on a flexible polyester substrate. The WE shown in FIG. 3 was constructed using an improvised method in which a base, such as n-butyl lithium, sodium hydride, or potassium tertiary butoxide was used.

To verify the pH-insensitive range of the AIM hydrogel, three IEs were prepared and tested against a standard calomel electrode (SCE) in a series of buffer solutions, each containing 100 mM of added sodium chloride. Square-wave voltammetry peak values were obtained from five measurements. An ideal AIM would show no deviation in peak potential, regardless of pH. As shown in Table 10 below, the IEs tested (EL1, EL2, EL3) show stability across the pH scale with varying sensitivity. In the biologically relevant range on pH 7.5 to 6, there was at most 2 mV deviation.

Across a broader range, the deviation is larger, with electrodes showing a standard deviation of 2 or 3 mV for a range between pH 2 and pH 10. This error, given a slope of 58 mV/pH unit for the ASM, will determine the resolution achievable using the AIM for a given pH range. For example, an error of 6 mV translates to a pH measurement error of 0.1 unit.

TABLE 10 pH insensitivity of Ferrocene-hydrogel electrodes

| Buffer pH | Buffer component | EL 1 | EL 2 | EL 3 |
|---|---|---|---|---|
| 2 | hydrochloric acid | 227 | 227 | |
| 3 | phthalate | 237 | 233 | |
| 4 | phthalate | 231 | 229 | 223 |
| 4.1 | acetate | 229 | 229 | 227 |
| 5 | phthalate | 229 | 231 | 225 |
| 6 | phosphate | 227 | 227 | 227 |
| 7 | phosphate | 228 | 227 | 226 |
| 7.5 | HEPES | 227 | 227 | 225 |
| 8 | phosphate | | | 226 |
| 9 | borate | | | 221 |
| 10 | carbonate | | | 221 |
| | E (avg) | 229 | 229 | 225 |
| | E (st. dev.) | 3 | 2 | 2 |

The AIM hydrogels used to generate the results in Table 1 were a matrix of DMAA cross-linked with 5% PEG-diacrylate and containing 1% vinylferrocene by weight. EL1 and EL2 were polymerized as 20 wt % solids in gel; EL3 was polymerized as 25% solids in gel. The electrodes were SWV scanned five times in each buffer with a 90-second delay between scans. The reported value in Table 1 is the last measurement of the 5-scan series. The value for pH 7 buffers in Table 1 is the average of measurements taken at the beginning and at the end of the pH excursion.

Figure 4:
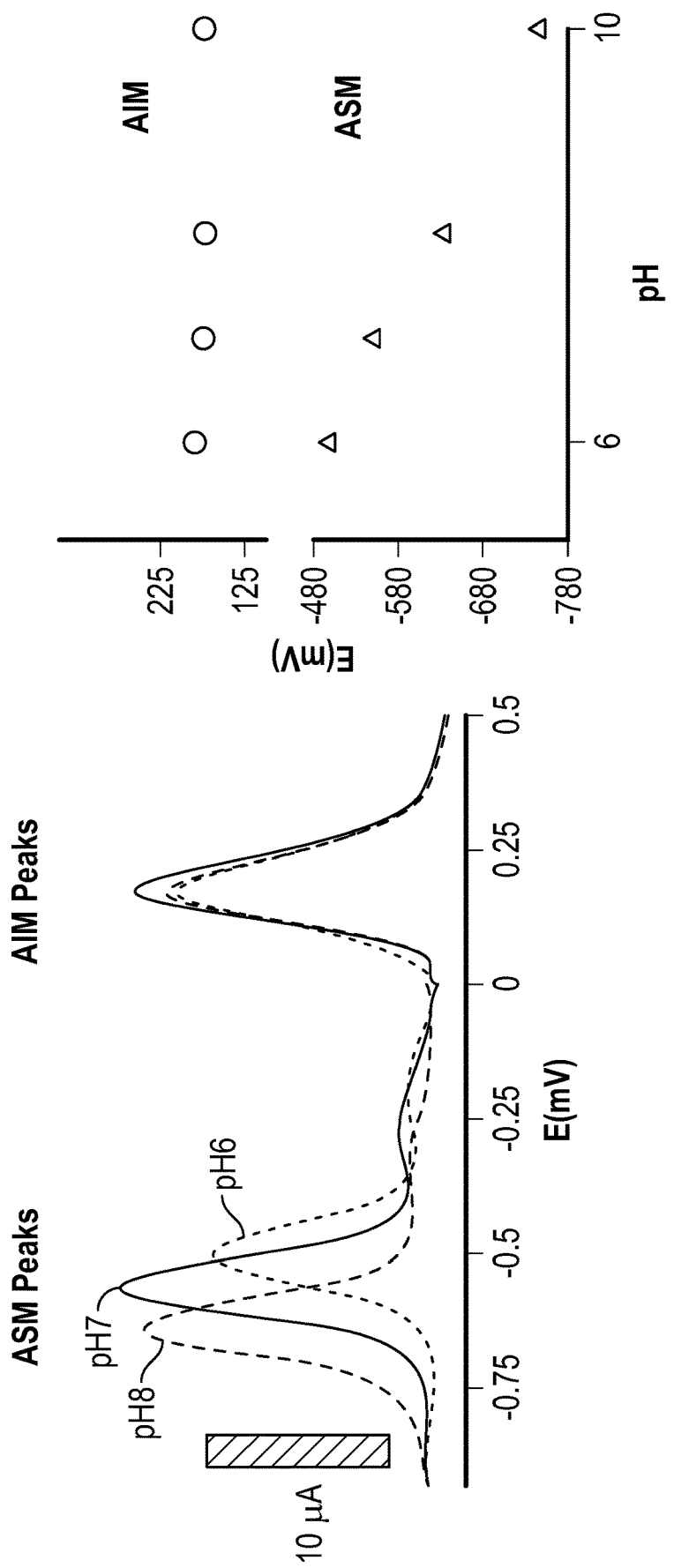
FIG. 4 shows the effect of pH changes on the WE (i.e. ASM) pH peak versus the IE (AIM, e.g. Fc) peak for a pH sensor comprising an AIM hydrogel of the invention as described in Example 1.

The characteristic response of the WE and IE to pH changes is shown in FIG. 4. Within experimental error, the AIM peaks measured in pH 6, 7, and 8 buffers were superimposable, whereas the ASM peaks showed an expected change as a function of pH.

The effect of changes in reference electrode on the WE-IE pair is shown in FIG. 5. In this case a pH 6 buffer was used. For the data labeled PRE (solid lines), the solid-state Ag/AgCl PRE shown in FIG. 3 was used. The ASM peak (left) and AIM peak (right) were separated by 675 mV. For the data labeled liquid-junction RE (dashed lines), a commercial Ag/AgCl reference electrode was used instead. The ASM and AIM peaks were separated by 671 mV. Despite a shift in nearly 100 mV of the reference potential, the differences between AIM and ASM peaks were nearly identical. In brief, these results demonstrate that, for this WE-IE pair of the invention, the AIM-ASM relationship is independent of the RE.

Example 2: Intrinsic pH Response of an All Solid State pH Sensor System

In conventional SWV, pH is correlated directly to the characteristic potential of a single WE. For an WE-IE pair, the difference in potential of these two electrodes is correlated with pH. In this example, two WE-IE pairs were deployed with a counter electrode made of thin stainless steel rod, and a screen-printed silver/silver chloride electrode served as the PRE. All sensor components were solid-state. As described above, the nature of the reference electrode is somewhat flexible, and the pH calibration curve takes into account only the difference between the AIM and ASM peak positions. In this case, calibration was generated for duplicate WE-IE pairs using 20 mM buffer and 100 mM sodium chloride at ambient temperature (22-24° C.). The results are shown in FIG. 6.

FIG. 6 shows the linear relationship of potential to pH for two separate WE-IE pairs. The potential in this case is the difference between the AIM and ASM peaks measured relative to a PRE. This can be considered a calibration curve: Using the slope and intercept, an unknown pH can be determined. The ASM-AIM potential difference ideally will depend only on pH, not upon the absolute potential of the PRE.

Example 3: Response of WE-IE Pair to Analyte Perturbations, e.g. Ionic Strength

Figure 7:
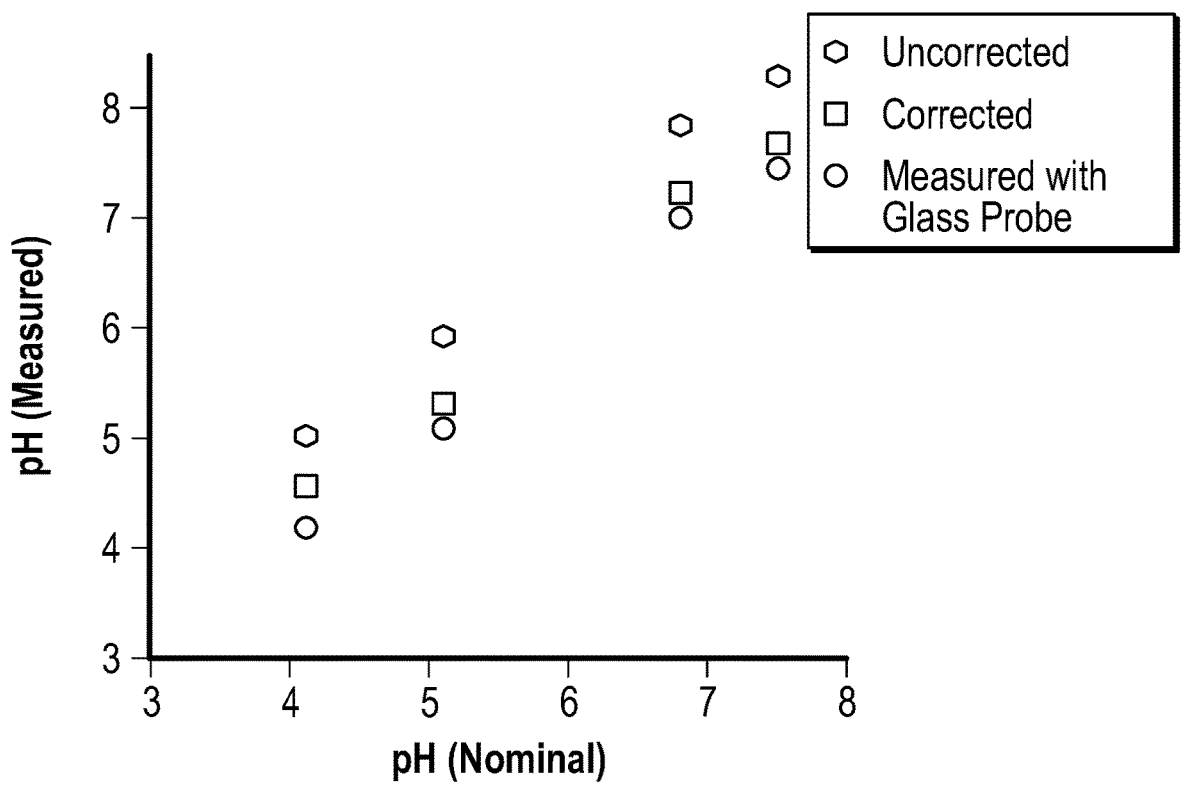
FIG. 7 shows the results comparing a WE-IE pair and a conventional glass pH electrode, as described in Example 3.

It is generally recognized that reference electrode potentials can be affected by changes in the analyte ionic strength. These changes can be compensated for in conventional potentiometric pH measurements by calibration at the expected ionic strength. With a WE-IE electrode pair of the present invention, changes in the RE (typically a PRE) potential affect the ASM and the AIM similarly. Thus the errors are self-canceling. This effect is shown in FIG. 7 where an ASM-AIM pair is compared with a conventional glass pH electrode (Thermo Orion). A WE-IE pair was first calibrated in BDH reference standard buffers (VWR International) containing 100 mM of added salt (sodium chloride). Measurements were then made in 10 mM sodium chloride solutions, which caused the PRE potential to shift by 30 mV. The pH as measured with a calibrated glass pH probe is shown using open circles. The pH measured using a WE relative to an Ag/AgCl PRE and without any correction is marked with X. The error is due to the shift in the PRE. The AIM-corrected pH is shown with filled circles. The accuracy of corrected pH values shows that, compared with the PRE, the AIM is much less sensitive to ionic strength. In summary, these results demonstrate that a WE-IE pair of the invention compensates for ionic strength effects on the CRE or PRE.

Example 4: PVA-AQ (ASM) Chemistries

A suitable electrode for use in pH meters of the invention can be prepared from a hydrogel composed of polyvinylalcohol covalently bonded to an anthraquinone derivative (PVA-AQ). PVA-AQ was synthesized using diethyl amino methyl polystyrene: a polymeric base commonly used in organic synthesis reactions. This reaction generally requires approximately 48 hours to complete. To shorten the reaction time, the invention provides a method in which n-butyl lithium, sodium hydride and potassium tertiary butoxide are reacted; however, any of a number of bases commonly used in organic synthetic reactions may be substituted and reaction conditions modified as needed to make a desired PVA-AQ of the invention, including any substitution to change the reaction time and/or density of AQ functionalization. Accordingly, the methods and PVA-AQ chemistries of the present invention may be tailored by using several different bases to achieve the functionalization of PVA desired for a particular application. An exemplary synthesis of PVA-AQ using n-butyl lithium as a base is shown in Table 11.

TABLE 11

PVA-AQ Synthesis using n-butyl lithium

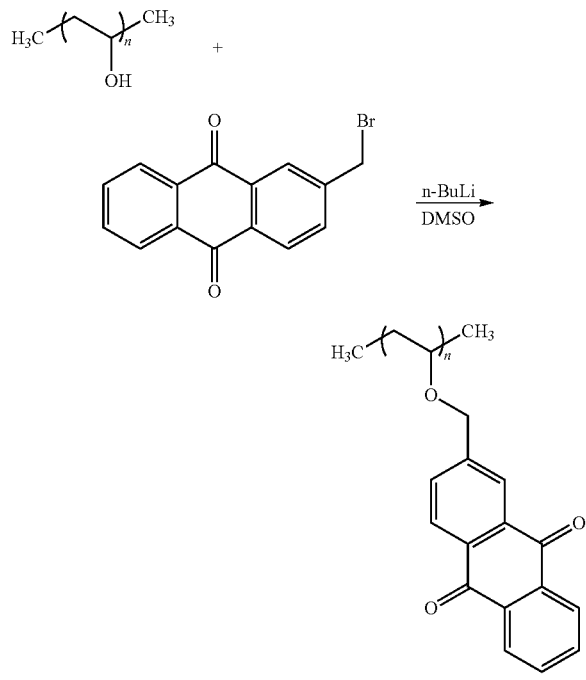

Synthesis of PVA-AQ Using N-Butyl Lithium as a Base

The procedure for preparing the PVA-AQ ASM of Table 10 is as follows. An oven dried 500 ml flask with a stir bar was purged with argon for 30 min. 1.77 g (0.042 mol) PVA was added to flask along with 300 mL dry DMSO added via cannula transfer. The system was maintained under positive argon pressure and heated to 50° C. in an oil bath while stirring with magnetic stir bar to dissolve PVA. After two hours, the flask was cooled to room temperature and 10.4 mL (0.0166 mol) n-butyl lithium was added. After 15 minutes, 5 g 2-bromomethyl anthraquinone was added. This was left to stir for 20 hours under argon at ambient temperature. The following day, the murky brown, crude reaction mixture was dropped into 10× volume stirring of 1,4-dioxane. The resulting solution is caramel-brown with pale yellow solids. This solution was left to stir for two hours and then vacuum filtered on glass fritted Buchner funnel. Alternately, the mixture above may be allowed to settle and the pale yellow solids could be separated after removing the solvent mixture by decantation. The solids were washed with acetone. The solids were again dissolved in DMSO, precipitated with 1, 4-dioxane and acetone to remove any unreacted bromomethyl anthraquinone. A hexane wash also used to help remove impurities.

B. Synthesis of PVA-AQ Using Sodium Hydride as the Base

An oven dried round bottom flask (flask 1) with a stir bar was left under argon for 30 min. 924 mg (21 mmol) of PVA was added to flask along with 50 ml of dry DMF added via cannula transfer. An oil bath was heated to 120° C., and the flask was placed in the oil bath to dissolve the PVA. Once the PVA is dissolved, the flask was removed from the oil bath and allowed to cool to room temperature. 20 ml dry DMF was added to a second oven dried flask (flask 2) via cannula transfer. Sodium hydride (400 mg, 10 mmols) was added to flask 2 and stirred. The contents of flask 2 were added to flask 1 via cannula transfer. The sodium hydride/PVA mixture of flask 1 appeared as a pale yellow suspension. After stirring for 20 min, bromomethylanthraquinone (300 mg, 1 mmol) was added to the reaction. After 5 minutes, the mixture turned deep yellow-brown with very little undissolved solids. This mixture was stirred for 90 min. 0.5 ml of water was added to quench the reaction and then stirred for an additional 30 minutes. 10.5 mL (10.5 mmols) of 1 M hydrochloric acid was then added to flask 1 which neutralized the deprotonated PVA to assist in solubilizing the mixture, the result of which caused the mixture to turn pale yellow. The contents of flask 1 were dropped into a new flask (flask 3) containing 1.5 L of acetone, and stirred for 15 minutes, during which a pale yellow precipitate formed. The precipitate was allowed to settle for 10 min and then decanted to reduce the precipitate's volume. The decanted precipitate was then vacuum-filtered on an ice bath. The solids were then washed with acetone and dried on vacuum.

Example 5: Preparation of Carbon Fiber Disks

The intended sensing sides of carbon fiber/polyvinyl ester disks (8.5 mm diameter) were sanded with 220 grit sandpaper. The sanded disks were then placed in a 100 ml beaker to which was then added 50 ml of hexanes (VWR) with sonication for 1 minute. The excess hexane was removed from the beaker. 50 ml of ethanol (VWR) were added to the beaker and sonicated continued for 1 minute, after which the excess ethanol was removed. A third washing step was completed by again adding 50 ml of ethanol to the beaker, sonicating the disks for 1 minute, and then removing the excess ethanol. The washed disks were then stored dry until use.

Example 6: Pre-Gel Mixture I

A 2 g hydrogel monomer solution was obtained by adding to a clean vial 0.06 g vinylferrocene, 0.06 g bisacrylamide, and 1.88 g DMAA. The contents of the vial were mixed to dissolve the vinylferrocene. Prior to storage, the headspace in the vial was purged with dry argon gas by gently blowing a stream of argon into the vial for 10 seconds. A cap was then placed on the vial, and the vial was stored in a freezer (−18 to −22° C.) for up to one week.

Example 7: Pre-Gel Mixture II

A 10 g hydrogel monomer solution was obtained by adding to a clean vial 0.10 g vinylferrocene, 1.0 g poly (ethyleneglycol) diacrylate, and 8.9 g DMAA. The contents of the vial were mixed to dissolve the vinylferrocene. Prior to storage, the headspace in the vial was purged with dry argon gas by gently blowing a stream of argon into the vial for 10 seconds. A cap was then placed on the vial, and the vial was stored in a freezer (−18 to −22° C.) for up to one week.

Example 8: In-Situ Hydrogel Formation with Carbon Fiber Electrodes

An oil bath was preheated to equilibrate at 75° C.). (+/−2° while being stirred with a wide stir bar at a rate of 50-100 rpm. 20 mg AIBN, 0.75 ml monomer solution, and 3.0 ml n-butanol was added to a 20 ml vial and mixed to dissolve the AIBN. Sanded and washed carbon fiber disks were stacked and added to the bottom of the vial, sanded faces up. A micro stir bar was added to the vial on top of the disks. The vial was then sonicated for 10 seconds. Using a stainless steel hollow needle, the solution in the vial was then sparged with argon for 1 minute and gently swirled at 20 second intervals to mix. The vial was then tightly capped and immersed in the oil bath so that the liquid contents of the vial are positioned 1 cm below the level of the oil. While in the oil bath, the liquid contents of the vial are mixed via the micro stir bar at a rate of approximately 50-100 rpm to gently agitate the solution without dislodging the carbon fiber disks. Gelation occurs after being in the oil bath for approximately 20 and 60 minutes, and is visible by immobilization of the micro stir bar. After 90 minutes total of being in the oil bath, the vial is removed and allowed to cool to ambient temperature.

Example 9: Washing and Storage of Hydrogel Electrodes

A metal spatula is used to break up the hydrogel solution so that the carbon fiber disks are dislodged. 15 ml of ethanol (95%) is added to the vial containing the carbon fiber disks, the vial then being stirred and mixed for 12-18 hours to allow the hydrogel solution to swell. The excess ethanol and swollen hydrogel is then removed from the vial. A 15 ml ethanol/water solution (1:1) is added to the disks inside the vial and stirred for 2 hours, after which the excess solution is removed from the vial. 15 ml of water is then added to the disks inside the vial and stirred for an additional 2 hours.

Using a razor, excess hydrogel is removed from the surface of each electrod by gently scrapting across both the surfaces and edges. The electrodes are then dried on paper (Kimwipe) for 10 minutes. The electrodes are then transferred to a clean, screw-cap vial that has been labeled.

Example 10: Preparation of a Ferrocene/PVA Acetal Using Ferrocenecarboxaldehyde With reference to Table 12, polyvinyl alcohol (2.0 gm, 4.55×10-2 equivalents) was dissolved in 1-methyl-2-pyrrolidinone (NMP, 50 mL) by stirring at room temperature overnight. Ferrocenecarboxaldehyde (500 mg, 2.34×10-3 moles) was then added to this stirred solution. Concentrated hydrochloric acid (1.0 mL) was then added and the resulting solution and stirred at room temperature for 48 hours. The polymer was precipitated by slow addition of the NMP solution to vigorously stirred ethyl acetate (250 mL). After the addition was complete, the ethyl acetate was decanted from the polymer which was subsequently stirred in ethyl acetate (250 mL ea.) twice to remove remaining NMP and unbound ferrocenecarboxaldehyde. The polymer was isolated by filtration, washed with ethyl acetate and then dried under vacuum.

TABLE 12

Ferrocene/PVA Acetal Compound

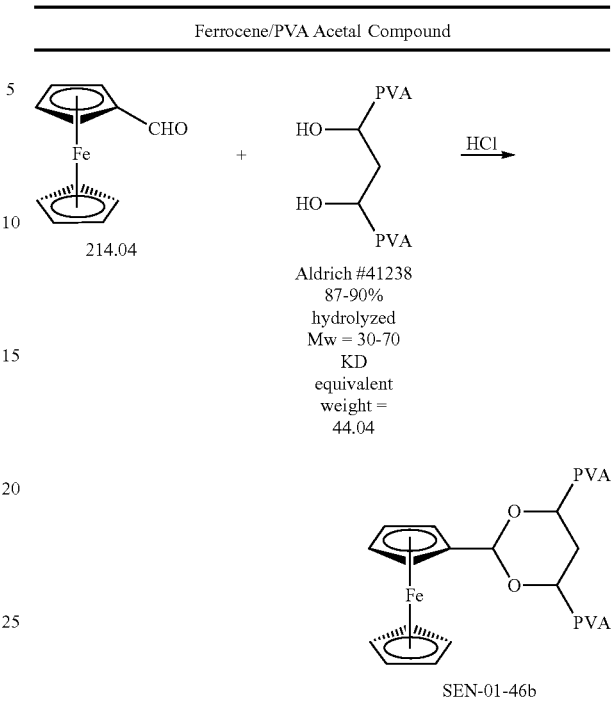

Example 11: Ferrocene/PVA Acetal Hydrogel Formation on Carbon Fiber Material SEN-01-46b is applied as a solution to a prepared carbon fiber disk, and subsequently dried and cured to render it insoluble.

Alternatively, an SEN-01-46b solution is first mixed with a pure PVA solution to adjust the mol % concentration of ferrocene. The adjusted SEN-01-46b solution is then applied to a prepared carbon fiber disk. A crosslinking agent selected from the group consisting of maleic anhydride, maleic acid, glutaraldehyde, diioscyanate, divinyl ether, periodate, or any generic dialdehyde, is then added to the solution to facilitate formation of the hydrogel on the prepared carbon material.

The invention claimed is:
1. A cross-linked hydrogel material, comprising an analyte-insensitive material-containing (AIM-containing) monomer, and at least one crosslinking monomer selected from the group consisting of i) methylene(bis)acrylamide, and ii) poly(ethyleneglycol)diacrylate, and comprising a first stoichiometric ratio of triethyleneglycol methyl ether methacrylate:AIM-containing monomer:methylene(bis)acrylamide, or comprising a second stoichiometric ratio of triethyleneglycol methyl ether methacrylate:AIM-containing monomer : poly(ethyleneglycol)diacrylate, either of the first or second stoichiometric ratios being from approximately 1000:1:5 to approximately 1000:1:20, or from approximately 1000:10:5 to approximately 1000:10:20.
2. The material of claim 1, wherein the AIM-containing monomer comprises polymerizable monomers suitable for use in forming a hydrophilic, cross-linked gel immobilized on the surface of a substrate of an indicator electrode (IE).
3. The material of claim 1, wherein the AIM-containing monomer comprises a pre-formed polymer to which is attached a ferrocene derivative or other suitable redox active, analyte insensitive compound.

4. The material of claim 3, wherein the pre-formed polymer is polyvinyl alcohol or partially hydrolyzed polyvinylacetate.

5. The material of claim 4, wherein the redox active material is ferrocene or substituted ferrocene.

6. The material of claim 5, wherein the attachment of the ferrocene or substituted ferrocene to either the pre-formed polymer or the redox active material is by an acetal linkage between the polyvinyl alcohol or partially hydrolyzed polyvinyl acetate and an aldehyde substitution on the ferrocene or substituted ferrocene of the redox active material.

* * * * *